United States Patent
Badger et al.

(10) Patent No.: US 6,660,112 B1
(45) Date of Patent: Dec. 9, 2003

(54) METHOD FOR MANUFACTURING EXPLOSIVE DEVICE HAVING SELF-REMEDIATING CAPACITY

(75) Inventors: Farrell G. Badger, Mapleton, UT (US); Brendan M. Welch, Farmington, CT (US); Ronald D. Thomas, Woodland Hills, UT (US); Lyman G. Bahr, Payson, UT (US); Dean F. Richards, Pleasant Grove, UT (US)

(73) Assignee: The Ensign-Bickford Company, Simsbury, CT (US)

( * ) Notice: Subject to any disclaimer, the term of this patent is extended or adjusted under 35 U.S.C. 154(b) by 0 days.

(21) Appl. No.: 09/666,020

(22) Filed: Sep. 19, 2000

Related U.S. Application Data

(60) Division of application No. 08/743,460, filed on Oct. 18, 1996, now Pat. No. 6,120,627, which is a continuation-in-part of application No. 08/658,104, filed on Jun. 4, 1996, now abandoned, which is a continuation-in-part of application No. 08/687,092, filed on Jun. 4, 1996, now abandoned, which is a continuation-in-part of application No. 08/560,102, filed on Nov. 17, 1995, now abandoned, said application No. 08/658,104, is a continuation-in-part of application No. 08/560,074, filed on Nov. 17, 1995, now abandoned.

(51) Int. Cl.$^7$ ................................................ A62D 3/00

(52) U.S. Cl. .................... 149/108.8; 102/293; 588/202; 588/203

(58) Field of Search ............................... 588/202, 203; 149/108.8; 102/293

(56) References Cited

U.S. PATENT DOCUMENTS

| 2,330,110 A | 9/1943 | Buchan | 166/21 |
|---|---|---|---|
| 3,157,119 A | 11/1964 | Porter | 102/21.8 |

(List continued on next page.)

FOREIGN PATENT DOCUMENTS

| DE | 3818398 | 12/1989 | ........... A01B/79/00 |
|---|---|---|---|
| DE | 4141940 | 12/1993 | ............. F42D/5/04 |
| EP | 251320 | 1/1988 | ............. C02F/3/34 |
| EP | 512660 | 11/1992 | ............ A62D/3/00 |

(List continued on next page.)

OTHER PUBLICATIONS

Sidhoum et al., *Enhanced Alaline Hydrolysis—Propellant*, Cent. for Eny. Eng'g, Stevens Inst. of Tech., Hoboken, N.J., Jan. 1998, p. 87–98.*

(List continued on next page.)

*Primary Examiner*—Peter A. Nelson
(74) *Attorney, Agent, or Firm*—TraskBritt, PC

(57) ABSTRACT

Technology for in situ remediation of undetonated explosive material. An explosive apparatus contains an explosive material in close proximity with microorganisms. An explosive mixture capable of self remediation in the form of an explosive material is intermixed with microorganisms. The microorganisms are either mobile or temporarily deactivated by freeze drying until rehydrated and remobilized. The microorganisms are capable of metabolizing the explosive material. Examples of such microorganisms include Pseudomonas spp., Escherichia spp., Morganella spp., Rhodococcus spp., Comamonas spp., and denitrifying microorganisms. A bioremediation apparatus that contains microorganisms and prevents contact between the microorganisms and explosive material is joined with an explosive apparatus that houses a charge of explosive material. A barrier is actuated by mechanical, electrical or chemical mechanisms to release the microorganisms into the explosive assembly to enable the microorganisms to begin metabolizing the explosive material, when the explosive apparatus is joined with the bioremediating apparatus. If the explosive material fails to detonate, the explosive is remediated by the action of the microorganisms. Remediation includes both disabling of the explosive material and detoxification of the resulting chemical compositions.

91 Claims, 16 Drawing Sheets

U.S. PATENT DOCUMENTS

| | | | | |
|---|---|---|---|---|
| 3,710,718 | A | 1/1973 | Grant | 102/23 |
| 4,016,117 | A | 4/1977 | Griffin | 260/17.4 |
| 4,044,684 | A * | 8/1977 | Gaggini et al. | 102/370 |
| 4,064,941 | A | 12/1977 | Smith | 166/300 |
| 4,108,728 | A | 8/1978 | Spinner et al. | 195/127 |
| 4,351,729 | A | 9/1982 | Witt | 210/603 |
| 4,365,557 | A * | 12/1982 | Couture et al. | 102/341 |
| 4,826,601 | A | 5/1989 | Spratt et al. | 210/610 |
| 4,845,034 | A | 7/1989 | Menger et al. | 435/167 |
| 4,919,813 | A | 4/1990 | Weaver | 210/603 |
| 4,925,552 | A | 5/1990 | Bateson et al. | 210/150 |
| 4,929,552 | A | 5/1990 | Gold et al. | 435/128 |
| 4,961,381 | A | 10/1990 | McLaughlin | 102/319 |
| 4,968,427 | A | 11/1990 | Glanser et al. | 210/610 |
| 5,011,614 | A | 4/1991 | Gresser et al. | 210/761 |
| 5,062,956 | A | 11/1991 | Lupton et al. | 210/611 |
| 5,071,755 | A | 12/1991 | Nelson et al. | 210/611 |
| 5,085,998 | A | 2/1992 | Lebron et al. | 435/262 |
| 5,120,441 | A | 6/1992 | Jackson et al. | 210/602 |
| 5,139,365 | A | 8/1992 | Chesner | 405/129 |
| 5,139,776 | A | 8/1992 | Chazono et al. | 424/92 |
| 5,296,146 | A | 3/1994 | Jackson et al. | 210/602 |
| 5,302,285 | A | 4/1994 | Attaway et al. | 210/605 |
| 5,314,821 | A | 5/1994 | Tyndall | 435/252.1 |
| 5,370,845 | A | 12/1994 | Miller et al. | 422/186.3 |
| 5,387,271 | A | 2/1995 | Crawford et al. | 71/9 |
| 5,392,860 | A | 2/1995 | Ross | 166/376 |
| 5,414,198 | A * | 5/1995 | Brodman et al. | 588/203 X |
| 5,420,035 | A | 5/1995 | Tyndall | 435/252.1 |
| 5,449,618 | A * | 9/1995 | Tyndall et al. | 588/203 X |
| 5,455,173 | A | 10/1995 | Crawford et al. | 435/264 |
| 5,478,743 | A | 12/1995 | Perkins et al. | 435/262.5 |
| 5,484,730 | A | 1/1996 | Tyndall et al. | 435/264 |
| 5,511,482 | A | 4/1996 | DiPietropolo | 102/426 |
| 5,518,919 | A * | 5/1996 | Tyndall | 588/202 X |
| 5,543,324 | A | 8/1996 | Rajan et al. | 435/252.4 |
| 5,578,487 | A * | 11/1996 | Tyndall | 588/203 X |
| 5,578,488 | A | 11/1996 | Tyndall et al. | 435/262.5 |
| 5,593,888 | A | 1/1997 | Glaze et al. | 435/262.5 |
| 5,610,062 | A | 3/1997 | Tyndall | 435/252.4 |
| 5,616,162 | A | 4/1997 | Crawford et al. | 71/9 |
| 5,711,020 | A * | 1/1998 | Wolfe et al. | 588/203 |
| 5,736,669 | A * | 4/1998 | Thomas et al. | 102/293 |
| 5,763,736 | A * | 6/1998 | Daume | 149/124 X |
| 5,763,815 | A * | 6/1998 | Thomas et al. | 102/293 |
| 5,814,514 | A | 9/1998 | Steffan et al. | 435/262 |
| 5,849,984 | A | 12/1998 | Kim et al. | 588/203 |
| 5,928,859 | A | 7/1999 | Nicklin et al. | 435/4 |
| 6,051,420 | A * | 4/2000 | Radtke et al. | 588/202 X |
| 6,066,772 | A * | 5/2000 | Hater et al. | 588/203 X |
| 6,084,150 | A | 7/2000 | Crawford et al. | 588/244 |
| 6,120,627 | A * | 9/2000 | Badger et al. | 149/108.8 |
| 6,121,506 | A | 9/2000 | Abel et al. | 588/200 |
| 6,156,560 | A | 12/2000 | Chun | 435/253.3 |
| 6,248,580 | B1 | 6/2001 | Spain et al. | 435/262.5 |
| 6,274,368 | B1 | 8/2001 | Nicklin et al. | 435/252.1 |
| 6,334,395 | B1 | 1/2002 | Badger et al. | 102/293 |
| 6,334,954 | B1 | 1/2002 | Crawford et al. | 210/610 |
| 6,348,639 | B1 | 2/2002 | Crawford et al. | 588/244 |
| 2002/0078849 | A1 | 6/2002 | Badger et al. | |

FOREIGN PATENT DOCUMENTS

| | | | |
|---|---|---|---|
| GB | 1396372 | 6/1975 | |
| NL | 8602985 | 6/1988 | B09B/3/00 |
| RU | 2039251 | 7/1995 | E21C/37/00 |
| WO | WO 91/15440 | 10/1991 | C05F/11/08 |
| WO | WO 95/01311 | 1/1995 | C02F/3/34 |
| WO | WO 95/03259 | 2/1995 | C05F/11/08 |

OTHER PUBLICATIONS

Sidhourn, Mohammed, et al., *Enhanced Alkaline Hydrolysis and Biodegradability Studies of Nitrocellulose–Bearing Missile Propellant*, Stevens Institute of Technology 87–98 (Jan. 1998).

Berry, D.F., et al., "Microbial Metabolism of Homocyclic and Heterocyclic Aromatic Compounds Under Anaerobic Conditions," 51(1) Microbiol. Rev. 43–59 (Mar. 1987).

Braun, Konstantin, et al., "Anaerobic Degradation of 2–Aminobenzoate (Anthranilic Acid) by Denitrifying Bacteria," 48(1) Appl. Environ. Microbiol. 102–107 (Jul. 1984).

Cartwright, N.J. et al., "Bacterial Degradation of the Nitrobenzoic Acids," 71 Biochem. J. 248–261 (1959).

Channon, H.J., et al., "The Metabolism of 2:4:6–trinitrotoluene ($\alpha$–T.N.T.)," 38 Biochem. J. 70–85 (1944).

Doyle, Richard C., et al., "Effect of Dairy Manure and Sewage Sludge on [14–C]–Pesiticide Degradation in Soil," 26(4) J. Agric. Food Chem. 987–989 (1978).

Federle, Thomas W., "Mineralization of Monosubstituted Aromatic Compounds in Unsaturated and Saturated Subsurface Soils," 34 Can. J. Microbiol. 1037–1042 (1988).

Fröslie, Arne, et al., "Ruminal Metabolism of DNOC and DNBP," 11 Acta Vet. Scand. 114–132 (1970).

Gorontzy, Thomas, et al., "Microbial Transformation of Nitroaromatic Compounds Under Anaerobic Conditions," 139 J. Gen. Microbiol. 1331–1336 (1993).

Goszczynski, Stefan, et al., "Isotopically Labelled Compounds for Hazardous Waste Site Cleanup Investigations: Part I. Synthesis of [phenyl–U–$^{14}$C] labelled 2,4–dinitro–6–sec–butylphenol (dinoseb) and [phenyl–U–$^{14}$C] labelled 4–n–propylphenol," 24(1) J. Labelled Compounds And Radiopharmaceuticals 35–42 (1991).

Gottschalk, Gerhard, Bacterial Metabolism 157–162 (2d ed. 1986).

Heinis, F.S., et al., "Verwijdering van Bodemverontreiniging," 39 PT/CIVIELE TECHNIEK 7–15 (1984).

Hallas, Laurence E., et al., "Microbial Transformation of Nitroaromatic Compounds in Sewage Effluent," 45(4) Appl. Environ Microbiol. 1234–1241 (Apr. 1983).

Jensen, H.L., et al., "Microorganisms that Decompose Nitro–Aromatic Compounds, With Special Reference to Dinitro–Ortho–Cresol," 17 Acta Agriculturae Scandinavica 115–126 (1967).

Kaake, Russell H. et al., "Bioremediation of Soils Contaminated with the Herbicide 2–sec–Butyl–4,6–Dinitrophenol (Dinoseb)," 58(5) Appl. Env. Microbiol. 1683–1689 (May 1992).

Kaplan, D.L., et al., "Thermophilic Biotransformations of 2,4,6–Trinitrotoluene Under Simulated Composting Conditions," 44(3) Appl. Environ. Microbiol. 757–760 (Sep. 1982).

Kaplan, David L., "Biotransformation Pathways of Hazardous Energetic Organo–Nitro Compounds," in Biotechnology And Biodegradation 155–180 (Kamely, D. et al., eds. 1990).

Kuhn, Elmar P., et al., "Anaerobic Degradation of Alkylated Benzenes in Denitrifying Laboratory Aquifer Columns," 54(2) Appl. Environ. Microbiol. 490–496 (Feb. 1988).

McBride, Kevin E., et al., "Metabolism of the herbicide bromoxynil by *Klebsiella pneumoniae* subsp. ozaenae," 52(2) Appl. Environ. Microbiol. 325–330 (Aug. 1986).

McCormick, Neil G., et al., "Microbial Transformation of 2,4,6–Trinitrotoluene and Other Nitroaromatic Compounds," 31(6) Appl. Environ. Microbiol. 949–958 (Jun. 1976).

Naumova, R.P., et al., "Possibility of Deep Bacterial Destruction of 2,4,6–Trinitrotoluene," 57 Mikrobiologiya 218–222 (1988).

Parris, George E., "Environmental and Metabolic Transformations of Primary Aromatic Amines and Related Compounds," 76 Residue Reviews 1–30 (1980).

Preuss, Andrea, et al., "Anaerobic transformation of 2,4,6–trinitrotoluene (TNT)," 159 Arch. Microbiol. 345–353 (1993).

Pumfrey, L., et al., "A Clostridium Species that Grows on 2,4,6–trinitrotoluene (TNT)," in Abstr. $93^{rd}$ Gen. Meet. Am. Soc. Microbiol. 421, Abs. No. Q–414 (1993).

Rafii, Fatemah, et al., "Reduction of Nitroaromatic Compounds by Anaerobic Bacteria Isolated From the Human Gastrointestinal Tract," 57 Appl. Environ. Microbiol. 962–968 (1991).

Rafii, Fatemeh, et al., "Reduction of Azo Dyes and Nitroaromatic Compounds by the Same Extracellular Enzyme from *Clostridium perfringens*," in Abstr. $93^{rd}$ Gen. Meet. Am. Soc. Microbiol. 276 (1993).

Schink, Bernard, "Principles and Limits of Anaerobic Degradation: Environmental and Technological Aspects," in Biology Of Anaerobic Microorganisms 771–846 (Zinder ed. 1988).

Shieh, Chih–Shin, "Physical and Chemical Behavior of Stabilized Sewage Blocks in Seawater," 23(1) Environ. Sci. Technol. 121–125 (1989).

Simmons, Kathleen E., et al., "Oxidative Co–Oligomerization of Guaiacol and 4–Chloroaniline," 23(1) Environ. Sci. Technol. 115–121 (1989).

Smolenski, Walter J., et al., "Biodegradation of Cresol Isomers in Anoxic Aquifers," 53(4) Appl. Environ. Microbiol. 710–716 (Apr. 1987).

Spain, Jim C., et al., "Enzymatic Oxidation of p–Nitrophenol," 88(2) Biochemical And Biophysical Research Communications 634–641 (1979).

Stevens, Todd O., et al., "Biodegradation of Dinoseb (2–sec–Butyl–4,6–Dinitrophenol) in Several Idaho Soils with Various Dinoseb Exposure Histories," 56(1) Appl. Env. Microbio. 133–139 (Jan. 1990).

Stevens, Todd O., et al., "Selection and Isolation of Bacteria Capable of Degrading Dinoseb (2–sec–butyl–4,6–dinitrophenol)," 2 Biodegradation 1–13 (1991).

Stevens, Todd O., "Biodegradation of Dinoseb (2–sec–Butyl–4,6–Dinitrophenol) and Bioremediation of Dinoseb–Contaminated Soils" (Nov. 1989).

Tiedje, James M., et al., "The Ecology of an Anaerobic Dechlorinating Consortium," in Environmental Biotechnology 3–14 (Omenn ed. 1988).

Tratnyek, Paul G., "Abiotic Reduction of Nitro Aromatic Pesticides in Anaerobic Laboratory Systems Designed to Model Dissolved Organic Matter" (Aug. 1987).

Tratnyek, Paul G., et al., "Abiotic Reduction of Nitro Aromatic Pesticides in Anaerobic Laboratory Systems," 37 J. Agric. Food Chem. 248–254 (1989).

Tschech, Andeas, et al., "Methanogenic Degradation of Anthranilate (2–Aminobenzoate)," 11 System. Appl. Microbiol. 9–12 (1988).

Vlassak, K., et al., "Dinoseb as a Specific Inhibitor of Nitrogen Fixation in Soil," 8 Soil Biol. Biochem. 91–93 (1976).

Wallnöfer, P.R., et al., "Transformation of Dinitrophenol–Herbicides by Azotobacter Sp.," 12 Chemosphere 967–972 (1978).

Yang, Yan–Xi, et al., "Bacteria Transforming 2,4,6–trinitrotoluene (α–TNT) and Their Application," in 92 Chemical Abstracts 375, Abs. No. 134719 (1980).

Zeyer, Josef, et al., "Degradation of 0–Nitrophenol and m–Nitrophenol by a *Pseudomonas putida*," 32(2) J. Agric. Food Chem. 238–242 (1984).

Ziegler, K., et al., "Studies on the Anaerobic Degradation of Benzoic Acid and 2–Aminobenzoic Acid by a Denitrifying Pseudomonas Strain," 149 Arch. Microbiol. 62–69 (1987).

Ziegler, Klaus, et al., "Activation of Aromtic Acids and Aerobic 2–Aminobenzoate Metabolism in a Denitrifying Pseudomonas Strain," 151 Arch. Microbiol. 171–176 (1989).

Kaplan, David L., *Biotechnology and Bioremediation for Organic Energetic Compounds*, Organic Energetic Compounds, 373–416 (Marinkas, Paul L. ed. 1944).

John P. Knezovich et al., *Chemical and Biological Systems for Treating Waste Streams Contaminated with High Explosives*, paper submitted for JANNAF Safety and Environmental Protection Subcommitee Meeting in Tampa, Florida (Dec. 5–8, 1995).

John P. Knezovich et al., *Chemical and Biological Systems for Regenerating Activated Carbon Contaminated with High Explosives*, paper submitted to Proceedings Demin '94 in Luxembourg, Luxembourg (Nov. 14–16, 1994).

R. Boopathy et al., *Biological Transformation of 2, 4, 6—Trinitrotoluene (TNT) By Soil Bacteria Isolated from TNT—Contaminated Soil*, 47 Bioresource Technology 19 (1994).

R. Boopathy et al., "*Biotransformation of 2, 4, 6—Trinitrotoluene (TNT) By Co–Metabolism With Various Co–Substrates: A Laboratory–Scale Study*," 47 Bioresource Technology 205 (1994).

\* cited by examiner

METHOD FOR MANUFACTURING EXPLOSIVE DEVICE HAVING SELF-REMEDIATING CAPACITY

RELATED APPLICATIONS

This application, is a divisional application of U.S. patent application Ser. No. 08/743,460 that was filed on Oct. 18, 1996 (hereinafter "the Parent Application"), and that issued as U.S. Pat. No. 6,120,627 on Sep. 19, 2000. The Parent Application; is a continuation-in-part application of both U.S. patent application Ser. No. 08/658,104 that was filed on Jun. 4, 1996, now abandoned, which is a continuation-in-part of U.S. patent application Ser. No. 08/560,074 that was filed on Nov. 17, 1995, now abandoned and U.S. patent application Ser. No. 08/687,092 that was filed Jun. 4, 1996, now abandoned which is a continuation-in-part application of U.S. patent application Ser. No. 08/560,102 that was filed on Nov. 17, 1995, now abandoned.

This application discloses subject matter related to that disclosed in U.S. Pat. No. 5,736,669 that issued on Apr. 7, 1998, from U.S. patent application Ser. No. 658,995 filed on Jun. 4, 1996, and which is a continuation-in-part of U.S. patent application Ser. No. 560,527 that was filed on Nov. 17, 1995, and subject matter related to that disclosed in U.S. Pat. No. 5,763,815 that issued on Apr. 7, 1998, from, and U.S. patent application Ser. No. 658,142 that was filed Jun. 4, 1996, and which is a continuation-in-part of U.S. patent application Ser. No. 560,074, filed on Nov. 17, 1995.

This application is also related to a U.S. patent application that is being filed contemporaneously herewith and that is related to the same applications and in the same manner as those set forth above for this application.

BACKGROUND OF THE INVENTION

1. The Field of the Invention

The present invention is directed to systems, apparatus, and methods for remediating explosives. More particularly, the present invention is directed to the remediation of explosives which have not detonated.

2. Background Art

Explosive charges are inherently dangerous in a number of respects.

Inadvertent detonation poses risks of severe personal injury or death, as well as of substantial property destruction and consequential losses. Explosive charges are, in addition, comprised of material substances, which even when not consolidated in a shape capable of performing as a detonatable explosive charge, may be toxic and thus potentially injurious to human health and to complex as well as simple plant and animal life.

Explosive charges that are not securely stored in a supervised manner, or isolated from the environment and from indiscriminate access by human and animal life forms, thus present both safety and environmental hazards.

Such hazards are pointedly apparent where an explosive charge fails to detonate after the explosive charge has been installed for that purpose during activities pertaining to mining, construction, or to seismic surveying. Fortunately, installed explosive charges that do not detonate as planned are usually locatable and often recoverable through the expenditure of reasonable efforts and without safety risks to personnel. On the other hand, there do routinely arise circumstances in which undetonated explosive charges of this type are not recovered or simply cannot be recovered. Then, the risks are present that the undetonated explosive charge could at some subsequent time be detonated inadvertently or become a source of potentially harmful contaminants.

As an example, seismic survey data used to ascertain the nature of subsurface ground structures is routinely obtained by recording and analyzing shock waves that are propagated into the ground and produced by detonating explosive charges. The shock waves are then monitored during transmission through the ground. In this role, such seismic charges are usually utilized in large sets, installed as an array of individual seismic charges at widely disbursed locations. The seismic charges are interconnected with detonation equipment for remote detonation, either simultaneously or in sequence.

Seismic charges for such surveys can be detonated either above or below the surface of the ground. In either case, it is not uncommon that at least one of any set of such seismic charges does not detonate as intended. Such failures may be caused by defects in the explosive charge itself, by damage caused during installation, by faulty detonation equipment, or by the failure of personnel in the field to make effective interconnections between that detonation equipment and each seismic charge in the installed set.

When a seismic charge installed above the ground fails to detonate as intended, it is usually possible to locate and safely recover the undetonated seismic charge. Nonetheless, circumstances do exist where the detonation of a set of seismic charges installed above the ground dislocates one of the undetonated seismic charges in the set, directing that undetonated seismic charge into a terrain in which the charge cannot be located or cannot be recovered easily. Responsible seismic crews naturally are trained to exercise all reasonable efforts to recover undetonated seismic charges that are located on the surface of the ground, but even the most rigorously indoctrinated and enthusiastic seismic personnel cannot guarantee that all undetonated seismic charges installed above the ground are ultimately recovered.

Aside from the human factor involved, the intervention of severe weather conditions, such as sandstorms, blizzards, tornadoes, or hurricanes, can impede efforts to recover undetonated seismic explosives. Some such weather conditions offer the prospect of even altering the terrain, thereby burying the undetonated seismic charge temporarily or for a substantial duration. Floods can cover the seismic survey site, removing or obscuring undetonated seismic charges. In the extreme, geological surface changes, such as mudslides, rockfalls, and fissures caused by earthquakes, by heavy weather, or even by seismic survey activity itself, can preclude the recovery of undetonated seismic charges, and even obscure the understanding that any seismic charge has failed to detonate.

The safety risks and environmental hazards posed by loose, undetonated explosive charges will be present where any undetonated seismic charge remains unrecovered after the detonation of the set of seismic charges of which it was a part.

The likelihood that an undetonated seismic charge will be abandoned is greatest, however, relative to the conduct of seismic survey activity based on the detonation of seismic charges installed below the surface of the ground. In such sub-surface seismic detonation activity, a series of deep boreholes are drilled into the earth or rock at predetermined locations that are intended to maximize the data to be derived from the shock waves promulgated from the detonation of the seismic charges. A seismic charge is placed at the bottom of each borehole and then shut in the borehole in a relatively permanent manner using a concrete or a sealing compound, such as bentonite. The balance of the borehole is then backfilled with loose soil and rock, a process which alone accounts for the majority of failed seismic detonations. Backfill materials have an understandable tendency to break the detonating cord leg wires or non-electric transmission line that interconnects the installed seismic charge at the bottom of the borehole with detonating equipment located above the ground. If a seismic charge installed below the ground fails to detonate, the easy removal of the undetonated seismic charge is seriously impeded by yards of backfill and the cured concrete or sealing compound in which the seismic charge was embedded at the bottom of the original borehole. Removing such an installed seismic charge by reexcavating the original borehole or by digging around the original borehole to avoid the sealing compound is extremely laborious and time consuming, potentially unsafe, and in many circumstances virtually impossible.

Thus, in conducting seismic survey activities, particularly seismic survey activities involving the detonation of seismic charges below the surface of the ground, undetonated seismic charges are regularly abandoned in the field. Frequently, even the precise location of undetonated seismic charges cannot be pinpointed. The risks from undetonated explosive charges installed in the ground endure for a substantial time, usually exceeding the durability of ground surface warning signs, fencing, or the continued possession and control of access to the site by an original owner. Eventually, the pressure of human population growth may render the site attractive for civil or industrial activities that would not be consistent with buried undetonated explosive charges.

The associated dangers include first that of an accidental detonation at some future time. Less dramatic, but certainly of longer duration, are risks presented by the material substance of those undetonated charges. Once released from the confines of the casing of an explosive assembly, the explosive material therein may cease to present any risk of explosion. This type of release of explosive materials can occur through corrosion of the casing through the action of ground water, the fracture of the casing during careless installation, or the shifting of the ground structure at the location at which the undetonated seismic charge was abandoned. In due course, the prolonged effect of these forces in combination with surface erosion or subsurface fluid migration can disburse over a large area the material of a fractured explosive charge. That material may constitute a potentially problematic contaminant. Even if detected, remedial activities may be required to contain and possibly eliminate the contaminant.

Nonetheless, no practical methods exist for reliably remediating the risks posed by undetonated explosive charges, particularly where those undetonated explosive charges are originally installed below the surface of the ground.

SUMMARY OF THE INVENTION

It is thus the broad object of the present invention to protect public health and safety from risks arising from incidents of abandoned undetonated explosive charges.

Accordingly, it is a related object of the present invention to eliminate the possibility of detonation of abandoned explosive charges.

It is a complementary object of the present invention to reduce the likelihood that abandoned undetonated explosive charges will contribute to environmental pollution.

Thus, it is a specific object of the present invention to provide apparatus, systems, and methods for remediating in situ any installed explosive charge that fails to detonate as intended.

It is a particular object of the present invention to provide such apparatus, systems, and methods as are capable of reliably and safely remediating an undetonated explosive charge abandoned in the ground.

Yet a further object of the present invention is to provide such apparatus, systems, and methods as are capable of remediating an undetonated explosive charge, even if the location of the explosive charge cannot be ascertained with any degree of certainty.

These and other objects and features of the present invention will become more fully apparent from the following description and appended claims, or will be appreciated by the practice of the invention.

To achieve the foregoing objects, and in accordance with the invention as embodied and broadly described herein, apparatus, systems, mixtures and methods are provided that remediate in situ an undetonated explosive utilizing the biological activity of microorganisms.

In one form, an apparatus incorporating teachings of the present invention includes a quantity of explosive material and microorganisms that are disposed in sufficient proximity to the quantity of the explosive material that the microorganisms can initiate bioremediation of the explosive material when the microorganisms are mobile. Similarly, an explosive mixture is formed by intermixing the microorganisms. and the explosive material. The explosive apparatus preferably has a shell that enables water to flow through the shell to contact the explosive material. The shell may for example have an open end, have holes or be water permeable.

The apparatus or mixture may also further comprise a mobilization means for mobilizing the microorganism to contact the explosive material. The mobilization means enables the microorganisms to initiate bioremediation of the explosive material or to continue bioremediating the explosive material. The terms "mobile" and "mobility" refer to the ability of the microorganisms to move, to be carried by the movement of a liquid, to be distributed to the explosive material or to be unrestricted in movement by a barrier that previously confined the microorganisms such that after the barrier is removed the microorganisms can contact the explosive material. The term "active" refers to the state of the microorganisms wherein the microorganisms can bioremediate explosives.

An example of a mobilization means that is useful with an explosive apparatus includes a rigid mechanical structure having a barrier to prevent contact of the microorganisms with the explosive material until the barrier is removed and the microorganisms are mobilized to contact the explosive material. The barrier can be removed by a mechanism that is mechanical, electrical and/or chemical. Other examples of mobilization means which can be utilized with an explosive apparatus or an explosive mixture include a mobilizing liquid such as water or a liquid with nutrients, a sufficient degree of porosity in the explosive material or the explosive mixture, and surfactants in the explosive material or mixture.

The microorganisms can be mobile or deactivated. Examples of deactivated microorganisms include microorganisms that have been dehydrated by air drying or by being lyophilized. The microorganisms are preferably freeze dried to increase the survivability of the microorganisms during the forming process wherein the explosive material and microorganisms are combined. More specifically, it is desirable to heat the explosive material to increase the moldability of the explosive material and to enable the microorganisms and explosive material to be easily intermixed; however, the heat can be lethal to the microorganisms as the microorganisms are placed or mixed in the explosive material. Accordingly, the microorganisms have preferably been prepared such that the microorganisms can be characterized in that the microorganisms are sufficiently resistant to heat that a significant portion of the microorganisms survive the intermixing or placement process even when the process occurs at a temperature of about 100° C.

The microorganisms can be disposed in close proximity to the explosive material or dispersed within the explosive material in many different forms. The microorganisms can be in various aggregations such as in pellets or in capsules. The aggregations can also be added without any processing of the microorganisms to form the microorganisms into a particular distinct form. Accordingly, the microorganisms can be present as a flake, granule, clump, powder or shard of a nutrient medium containing microorganisms. Nutrients, in addition to the explosive material, are generally necessary for the microorganisms to survive and grow. Binders are also often necessary and organic binders are preferred. Depending on the binder or nutrient utilized, one chemical can perform the function of both binder and nutrient. The thermal resistance of the microorganisms can also be increased by utilizing various thermal protection additives.

An example of a structure having a barrier to prevent contact of the microorganisms with the explosive material until the barrier is removed is provided by a bioremediation apparatus in combination with an explosive material. The bioremediation apparatus includes a storage means for releasably containing at least one type of microorganism capable of degrading explosive materials. Stored distinctly therefrom in the bioremediation apparatus is a reservoir means for releasably containing a liquid intended to be mixed with the microorganisms. The storage means is positioned proximate the reservoir means, usually in a relationship that is below the reservoir means in the anticipated installed orientation of the inventive apparatus. The bioremediation apparatus further includes a first valve means for delivering the liquid from the reservoir means to the microorganisms in a storage means. Doing so causes mobilization of the microorganisms. This occurs when a first valve means is opened. The first valve means is at least partially disposed within the reservoir means.

Additionally, the bioremediation apparatus of the present invention comprises a second valve means for delivering hydrated microorganisms to an associated, undetonated explosive material. The second valve means is operably linked to the first valve means and is at least partially disposed within the storage means.

The bioremediation apparatus is coupled in one embodiment of the present invention with an explosive apparatus that has an actuation means for opening the first valve means and the second valve means upon being coupled thereto. The actuation means for opening the valves can be achieved by either a mechanical or electrical mechanism. If the explosive material in the explosive apparatus fails to detonate, the explosive material will eventually be remediated by the action of the microorganisms released from the associated storage means.

Ideally, the remediation occurs in two respects. The explosive is disabled from inadvertent detonation. Subsequently, the material composition of the explosive material is rendered relatively nonharmful.

In another embodiment of the invention, microorganisms are releasably contained by gelatin, a substance that is self-effacing when contacted by microorganisms under favorable conditions. For example, gelatin may be used to fabricate the first valve means that retains liquid in the reservoir means of the bioremediation apparatus or the second valve means that retains the microorganisms in the storage means of the bioremediation apparatus.

In yet another embodiment, microorganisms are applied directly to the exterior of the explosive material or to the shell of an explosive apparatus.

BRIEF DESCRIPTION OF THE DRAWINGS

In order that the manner in which the above-recited and other advantages and objects of the invention are obtained, a more particular description of the invention briefly described above will be rendered by reference to specific embodiments thereof, which are illustrated in the appended drawings. Understanding that these drawings depict only typical embodiments of the invention and are not therefore to be considered to be limiting of the scope of the invention, the present invention will be described and explained with additional specificity and detail through the use of the accompanying drawings in which.

Figure 1:
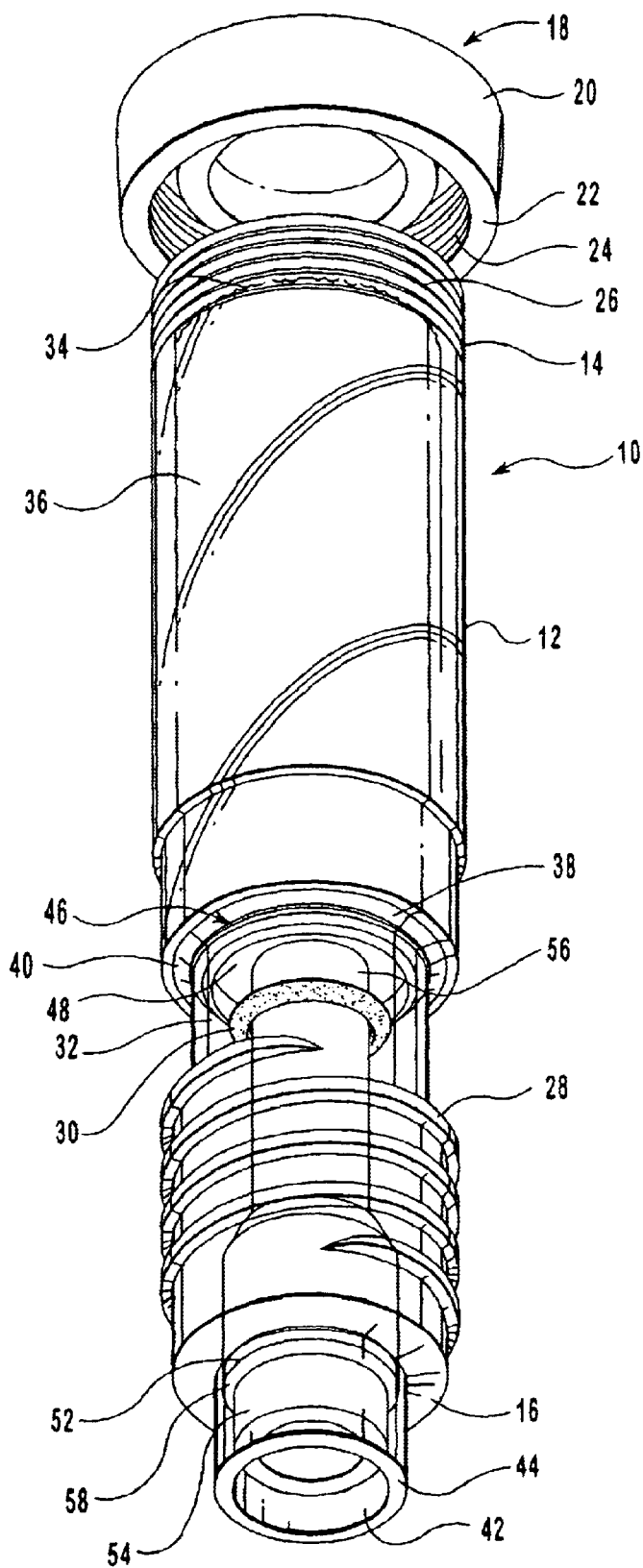
FIG. 1 is a perspective view of a first embodiment of a bioremediation apparatus incorporating teachings of the present invention.

A consortium of microorganisms within the scope of the present invention was deposited on May 23, 1996 with the American Type Culture Collection (hereinafter "ATCC") in accordance with the provisions of the Budapest Treaty on the International Recognition of the Deposit Microorganisms for the Purpose of Patent Procedure. The ATCC is located at 10801 University Boulevard, Manassas, Va. 20110-2209 U.S.A. The deposited consortium of microorganisms was assigned ATCC Designation No. 55784. For purposes of this disclosure, the microorganism consortium deposited with the ATCC and designated ATCC Designation No. 55784 is hereby incorporated by reference.

The microorganism consortium deposited with the ATCC was obtained from Richards Industrial Microbiology Laboratories, Inc. (hereinafter "RIML") located at 55 East Center, Pleasant Grove, Utah 84062 U.S.A. The microorganism consortium is identified at RIML by Product No. RL-247. Accordingly, microorganisms sold as RL-247 by RIML under the tradename RL-247 and assigned ATCC Designation No. 55784 are considered to be within the scope of the invention disclosed herein, whether or not constituent microorganisms therein are explicitly identified to any degree herein.

The microorganisms of the microorganism consortium are chosen for having a demonstrated ability to metabolize and degrade explosive materials in any way that contributes to the disabling of the explosive material or to the detoxification of the chemical components thereof. If microorganisms are selected that are both aerobic and anaerobic, bioremediation will occur in shallow and exposed surface locations, as well as in deep explosive boreholes. Ideally, the microorganisms selected for the microorganism consortium should be nonpathogenic and surfactant-producing, as this enhances the digestive action of the microorganism colony.

In one embodiment of a microorganism consortium chosen according to the teachings of the present invention, the Pseudomonas spp. are selected from the group consisting of aeruginosa, flourescens, acidovorans, mendocina, and cepacia. Any microorganisms of Pseudomonas spp. other than the microorganisms identified above are considered to be within the scope of the invention disclosed herein, provided that such microorganisms perform any of the functions described above having utility in the remediating of an explosive charge. Correspondingly, any microorganism is considered to be within the scope of the invention disclosed herein, provided the microorganism exhibits any utility relative to. the bioremediating of explosive materials.

Thus, the disclosure and incorporation herein of the microorganism consortium assigned ATCC Designation No. 55784 or the disclosure of the microorganism consortium available from RIML under the tradename RL-247, are but examples of microorganism consortiums within the teachings of the present invention and are not limiting of the microorganisms that may be selected for inclusion in a microorganism consortium according to the teachings of the present invention.

Various embodiments of explosives are set forth hereinbelow which are configured to enable microorganisms to bioremediate a quantity of explosive material. The microorganisms are disposed in sufficient proximity to the explosive material that the microorganisms initiate bioremediation of the explosive material when the microorganisms are mobilized.

The shelf lives of the explosive material and the microorganisms are increased by delaying the bioremediation activity of the microorganisms at least until the explosive is ready to be utilized. Accordingly, the preferred embodiments involve the use of microorganisms that are temporarily immobilized or have been blocked from contact with the explosive material until the explosive is to be positioned in the ground or after the explosive is in the ground. Configurations can also be utilized wherein the microorganisms are initially mobile when positioned relative to the explosive material, thereby enabling the microorganisms to immediately initiate bioremediation.

The embodiments of the invention designed to delay the bioremediation activity of the microorganisms until a set time utilize a mobilization means for mobilizing the microorganisms to contact the explosive material. The mobilization means enables the microorganisms to initiate bioremediation or continue bioremediation of the explosive material. Any mobilizing means can be utilized including mechanisms which are primarily mechanical, electrical, chemical or combinations thereof.

Figure 7:
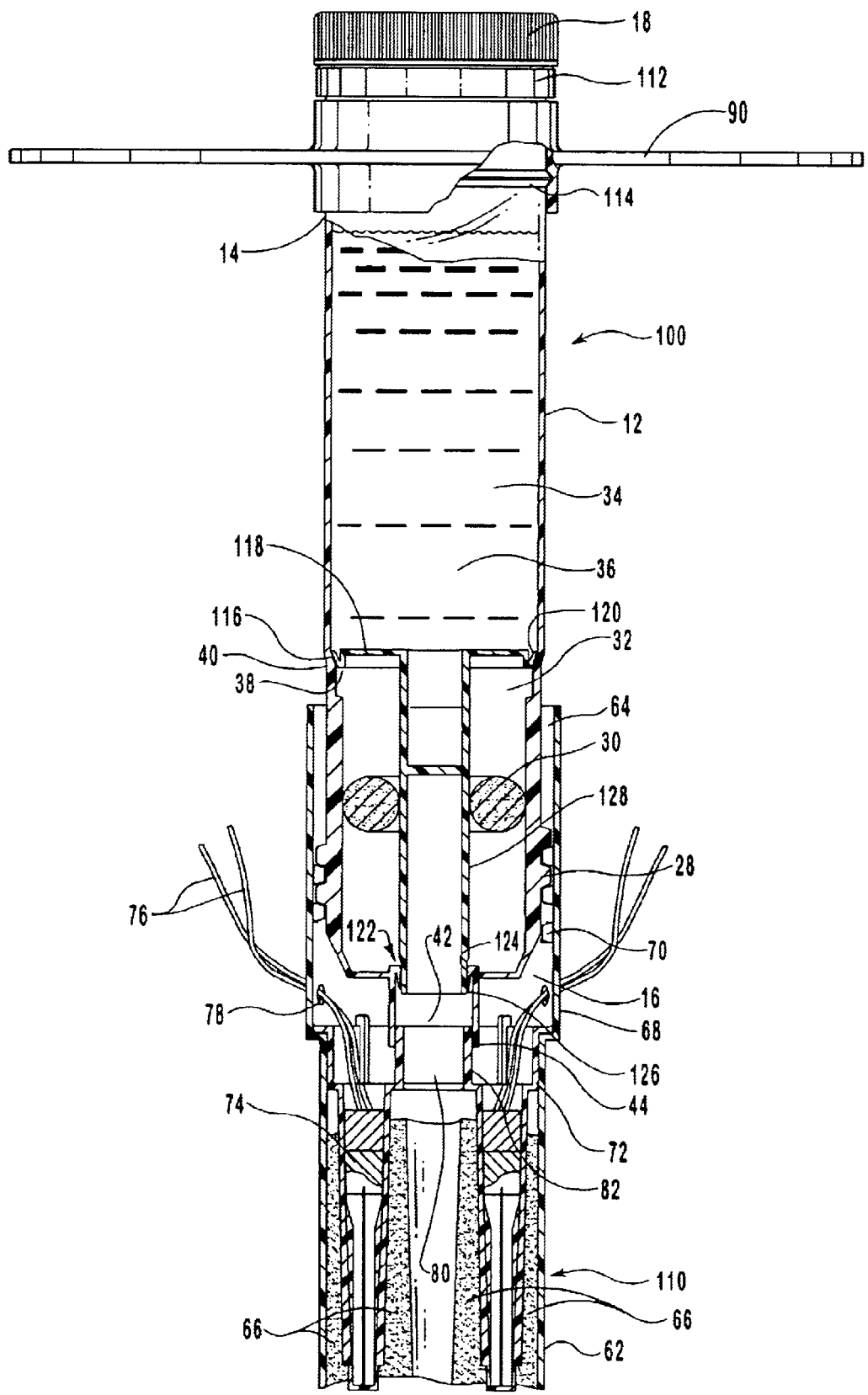
FIG. 7 is a partial cross-sectional elevation view like that of FIG. 4, but of a second embodiment of a bioremediation apparatus immediately incorporating teachings of the present invention immediately upon becoming fully coupled with an explosive apparatus.
Figure 8:
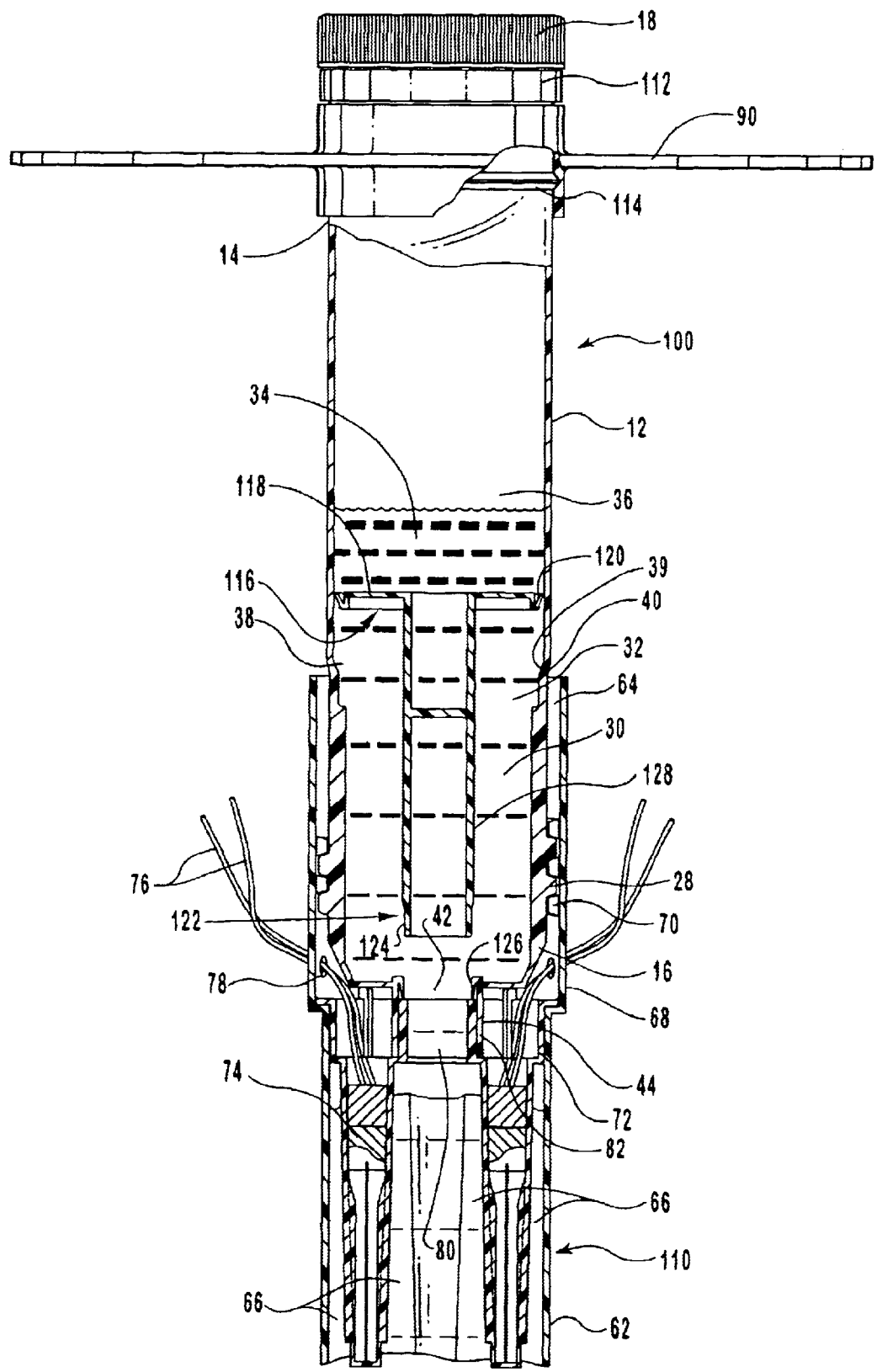
FIG. 8 is a partial cross-sectional elevation view like that of FIG. 6, but of the second embodiment of the bioremediation apparatus and the explosive apparatus illustrated in FIG. 7 at a time subsequent to that illustrated in FIG. 7 at which the explosive material in the explosive apparatus illustrated is contacted by hydrated microorganisms.
Figure 9:
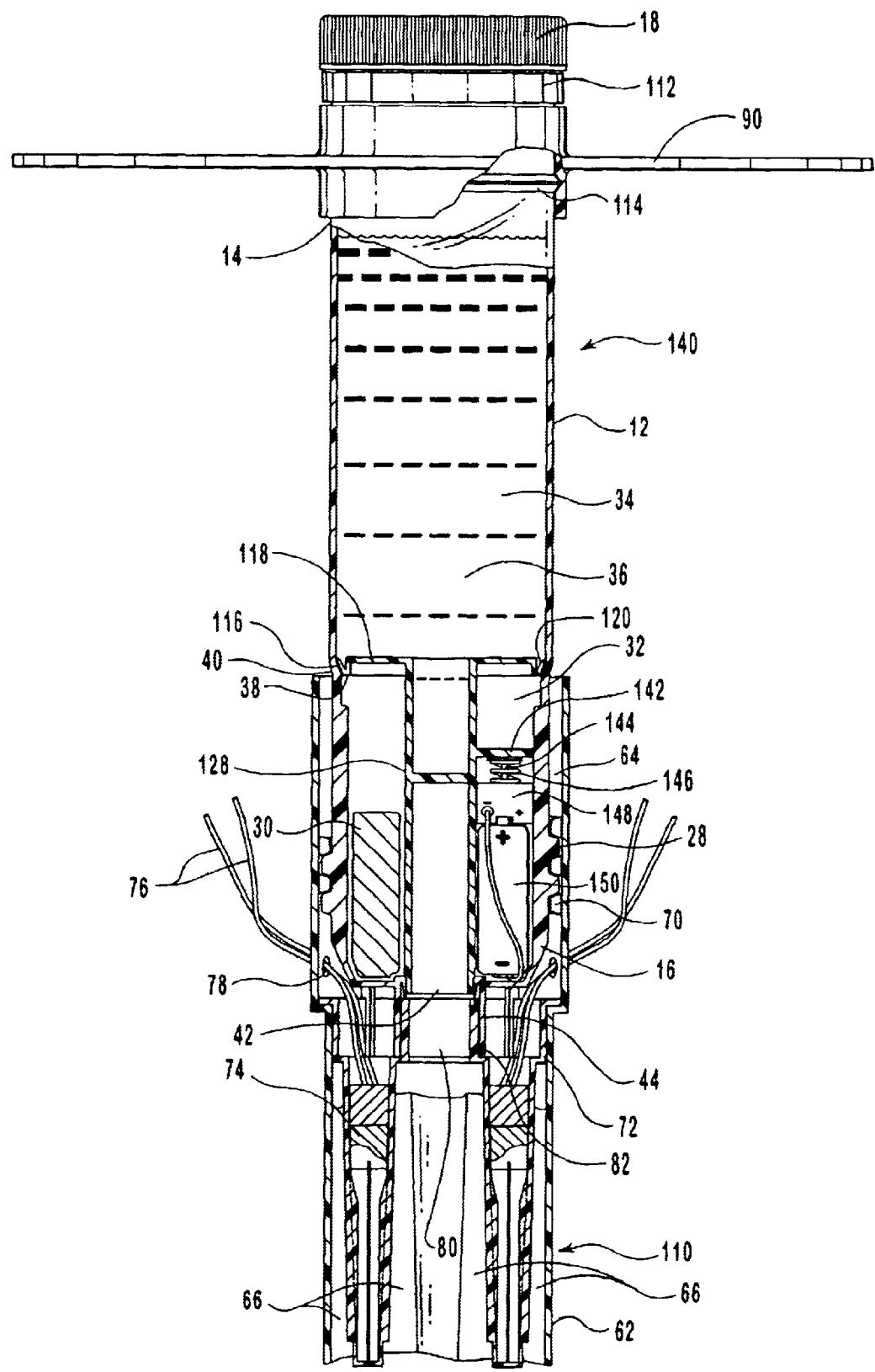
FIG. 9 is a cross-sectional elevation view of a third embodiment of an explosive apparatus that utilizes an electrical mechanism to control the mobilization of the microorganisms.

Examples of combinations of mechanical and chemical mechanisms utilized to mobilize the microorganisms are provided by the embodiment in FIGS. 1–6 and the embodiment in FIGS. 7–8. An embodiment is depicted in FIG. 9 that utilizes electrical, mechanical and chemical mechanisms to mobilize the microorganisms. In these embodiments, a rigid mechanical structure contains the microorganisms in a relatively immobilized condition or at least separate from the explosive material. Bioremediation of the explosive material is initiated when a barrier between the microorganisms and the explosive material is removed and the microorganisms are in an adequate quantity of a liquid to enable the microorganisms to be sufficiently mobile to flow into contact with the explosive materials.

A first embodiment of an apparatus employing principles of the present invention is illustrated in FIG. 1 as an explosive bioremediation apparatus 10. Bioremediation apparatus 10 includes a casing 12 having a top end 14 and a bottom end 16. Casing 12 is preferably formed from a material which is water resistant and is capable of withstanding extremes of temperature.

A cap 18 is inserted into top end 14 of casing 12. Cap 18 is preferably formed from a durable material that will withstand being driven down a borehole with a tamping pole. Cap 18 includes a cap top 20 and an external cap member 22 integrally extending from cap top 20 and having cap threads 24. Cap 18 is secured about top end 14 of casing 12 by engaging cap threads 24 with end threads 26 that are formed on the exterior of top end 14. Cap 18 may include an internal cap member with an O-ring or a foam seal so configured and positioned as to engage top end 14 of casing 12. This increases the security of the seal produced.

Cap 18 is but one example of a structure capable of functioning as a cap means for sealing the top end of a casing, such as casing 12. Another example of a structure capable of performing the function of a cap means according to the teachings of the present invention would be a casing without any external cap member, but rather having an internal cap member that is inserted into top end 14. Alternatively, bioremediation apparatus 10 could be provided with a structure that performs the foundation of such a cap means but is integrally formed with casing 12. Any such cap structure that is integrally formed with casing 12 from a plastic material should be constructed to withstand the impacts and pressure encountered in being pushed down a borehole.

Bioremediation apparatus 10 is configured at bottom end 16 of casing 12 for coupling with an explosive apparatus shown and discussed subsequently in relation to FIGS. 2–6 as housing a bioremediatable explosive material. Bioremediation apparatus 10 also has casing threads 28 on casing 12 that cooperatively engage correspondingly configured threads on the explosive apparatus to effect the intended coupling.

According to teachings of the present invention, microorganisms 30 capable of degrading explosive materials are stored in a storage means for releasably containing microorganisms. By way of example and not limitation, such a storage means within the scope of the present invention can take the form of a storage chamber 32 having sidewalls defined by casing 12. As shown in FIGS. 1–5, microorganisms 30 can be positioned on a ring formed from starch and flour, bran, or another similar nutrient material. The microorganisms 30 can be stored in a moist condition in storage chamber 32 or the microorganisms can also be lyophilized or freeze dried. Microorganisms 30 are preferably not mobilized until bioremediation apparatus 10 is actually coupled with an explosive apparatus which is preferably in the field at the time the seismic charge is to be placed in a borehole or at the time of the intended detonation of the charge in that explosive apparatus. In addition to a ring configuration, microorganisms 30 can be positioned in contact with materials such as starch, flour, or bran assuming any other arrangement.

Microorganisms 30 are mobilized by a liquid 34 stored in a reservoir means for releasably containing a liquid. Liquid 34 may be water or a nutrient medium that can feed microorganisms 30, but liquid 34 is resistant to freezing at ambient temperatures. By way of example and not limitation, a reservoir means within the scope of the present invention can take the form of a reservoir chamber 36. Reservoir chamber 36 has sidewalls defined by the interior of casing 12 and a top defined by cap 18. Reservoir chamber 36 also includes a liquid passage 38 defined by the interior of a neck 40. Neck 40 is an integral portion of casing 12 and has a diameter that tapers radially inwardly from the outer diameter of the sidewalls of reservoir chamber 36 to a smaller diameter, as observed to best advantage in FIG. 3.

Preferably, storage chamber 32 is positioned below reservoir chamber 36 in the anticipated orientation of bioremediation apparatus 10 when coupled to and installed with explosive apparatus 60. Storage chamber 32 is capable of communication with reservoir chamber 36 through liquid passage 38. Storage chamber 32 is provided with a bioremediation outlet 42 that is formed through bottom end 16 of casing 12 and through a sleeve member 44 which protrudes from bottom end 16 of casing 12. Accordingly, bioremediation outlet 42 is a portal or opening through casing 12 that is in communication with storage chamber 32.

Microorganisms 30 are mobilized by liquid 34 upon the opening of a first valve means for delivering liquid 34 from reservoir chamber 36 to storage chamber 32. By way of example and not limitation, a first valve means according to the teachings of the present invention can take the form of a first valve 46 which comprises the interior of neck 40 and a first valve member 48. A tapered end 50 is formed around the perimeter of first valve member 48 corresponding in dimension to the interior of neck 40. The cooperation of these structures forms a seal within liquid passage 38.

Figure 3:
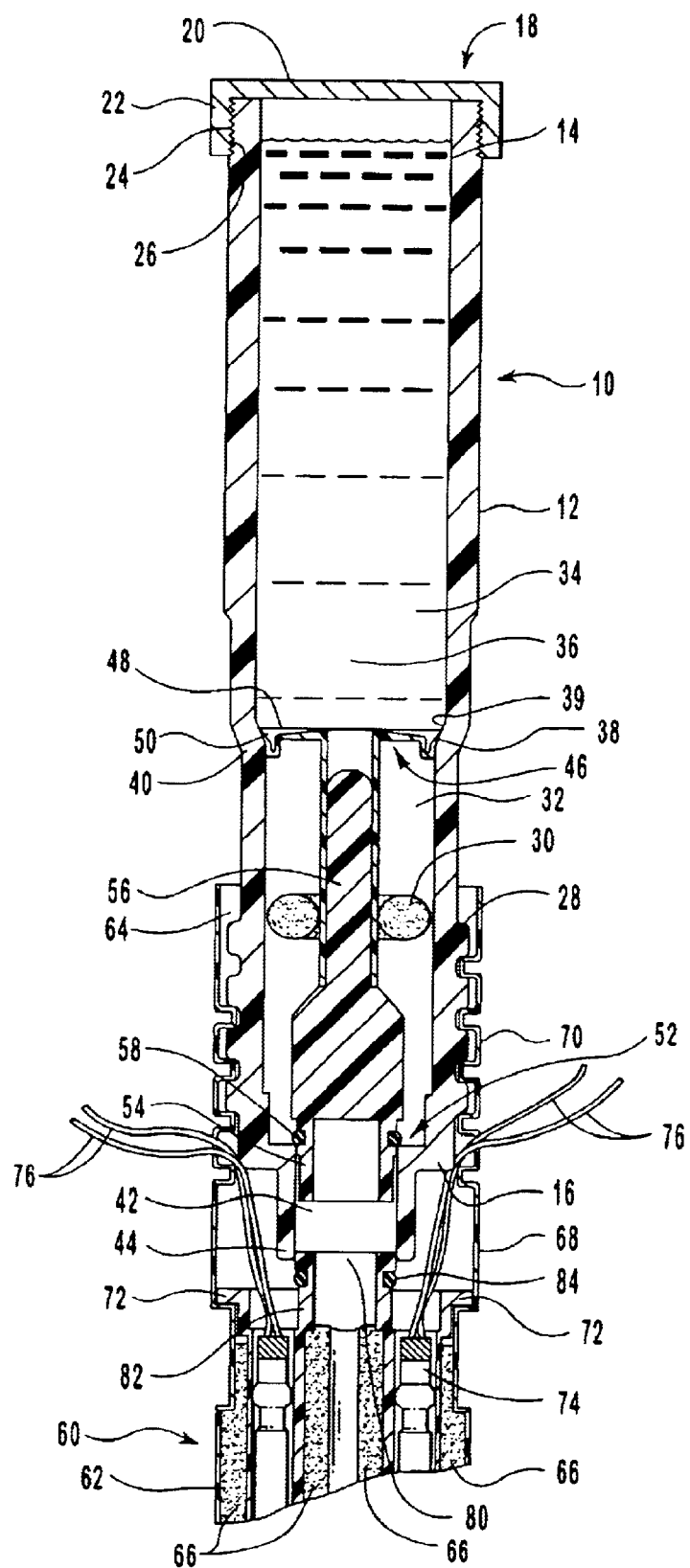
FIG. 3 is a cross-sectional elevation view of the bioremediation apparatus and the explosive apparatus illustrated in FIG. 2 taken along section line 3—3 shown therein.

When first valve 46, which is shown in FIG. 1, is closed as shown in FIG. 3, first valve 46 is at least partially disposed within reservoir chamber 36. More particularly, when first valve 46 is closed, first valve 46 is positioned between reservoir chamber 36 and storage chamber 32 and within liquid passage 38 with first valve member 48 defining the bottom of reservoir chamber 36 and the top of storage chamber 32. The seal formed within liquid passage 38 by first valve 46 thereby retains liquid 34 in reservoir chamber 36 until first valve 46 is opened.

Once mobilized or activated, microorganisms 30 flow out of storage chamber 32 upon the opening of a second valve means for delivering mobilized microorganisms to an explosive material in an explosive apparatus. By way of example and not limitation, a second valve means according to the teachings of the present invention can take the form of a second valve 52 which includes a second valve member 54 in combination with sleeve member 44. Second valve 52 defines the bottom of storage chamber 32 and is the lower end of a valve connector 56 that extends through bioremediation outlet 42 in sleeve member 44. Valve connector 56 has an upper end that is connected to first valve member 48.

When second valve 52 is closed as shown in FIG. 3, second valve 52 is at least partially disposed within storage chamber 32. More particularly, when closed, second valve 52 is positioned at the bottom of storage chamber 32 within bioremediation outlet 42. Second valve member 54 forms a seal with sleeve member 44 in bioremediation outlet 42, thereby to retain mobilized microorganisms 30 in storage chamber 32 until second valve 52 is opened. The security of the seal is increased by a valve O-ring 58, which encircles second valve member 54.

Valve connector 56 can best be seen in FIG. 3 to connect first valve member 48 and second valve member 54. The length of valve connector 56 is selected to enable first valve 46 and second valve 52 to open and close according to a predetermined timing relationship. Thus, first valve 46, second valve 52, and valve connector 56 can be configured to effect the simultaneous opening or actuation of first valve 46 and second valve 52. Alternatively, first valve 46, second valve 52, and valve connector 56 can be designed to actuate one of the valves in a delayed manner, after the other valve has been actuated. It may be desirable for example, to allow liquid 34 to contact microorganisms 30 by opening first valve 46, and only thereafter to open second valve 52.

When microorganisms 30 and liquid 34 are securely sealed in separate spaces as shown in FIG. 3, bioremediation apparatus 10 can be shipped and stored for long periods without any significant decrease in the bioremediating effectiveness thereof. The configuration of bioremediation apparatus 10 is designed for easy combination with a conventional explosive, such as a seismic booster.

Figure 2:
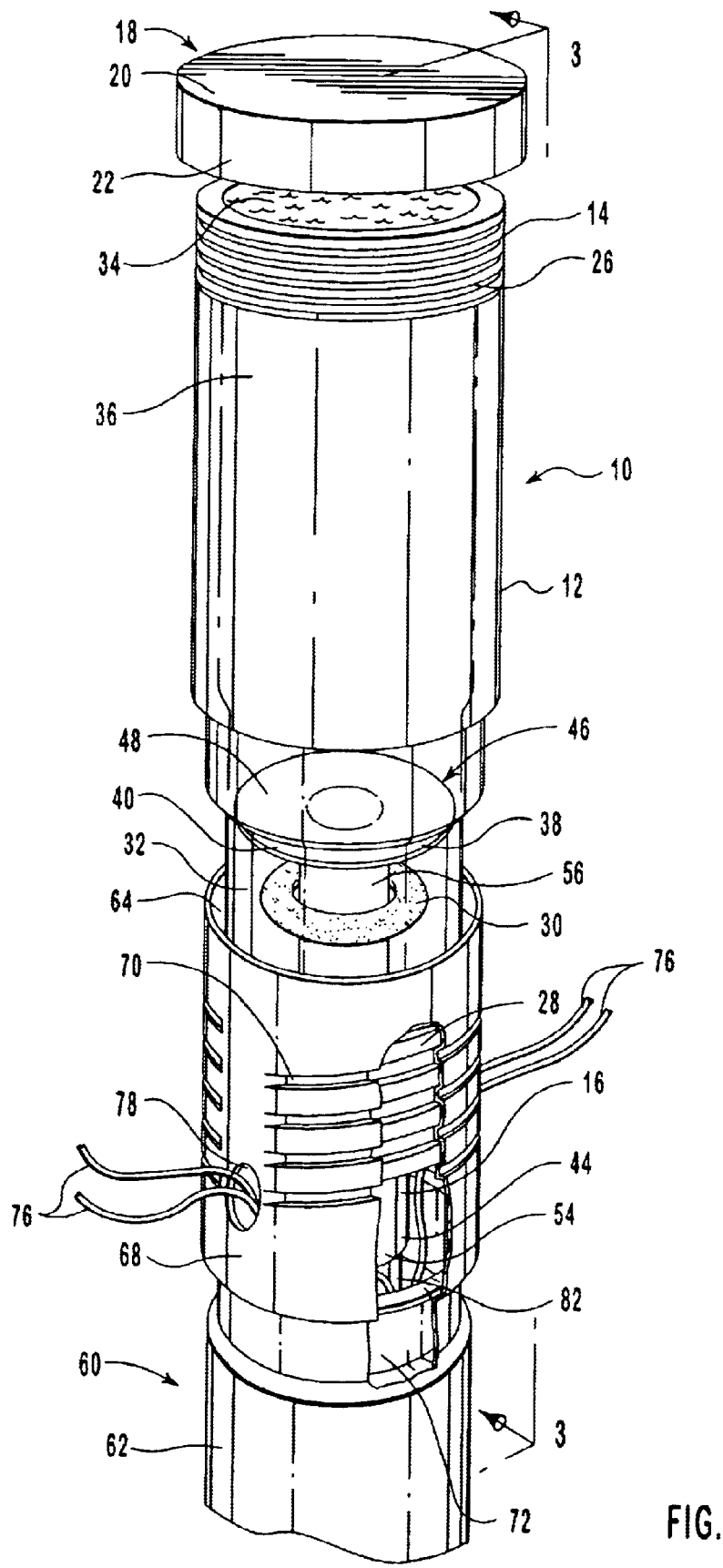
FIG. 2 is a perspective view in partial break-away of the bioremediation apparatus of FIG. 1 in the process of being coupled with an explosive apparatus in accordance with teachings of the present invention.

FIGS. 2 and 3 depict bioremediation apparatus 10 in the process of being coupled with an explosive apparatus 60. FIG. 2 is a perspective view, and FIG. 3 is a cross-sectional view taken along section line 3—3 of FIG. 2. As best illustrated in FIG. 3, first valve member 48 and second valve member 54 remain in closed positions when bioremediation apparatus 10 is initially threaded into explosive apparatus 60.

Explosive apparatus 60 comprises a shell 62 having an open end 64 and an explosive material 66 housed within shell 62. The interior of shell 62 is provided with shell threads 70 near open end 64. These cooperate with correspondingly configured casing threads 28 on bioremediation apparatus 10. Shell 62 can be formed from distinct components or as an integral structure as shown.

The combination of casing threads 28 and shell threads 70 together serve as an example of a coupling means for coupling a bioremediation apparatus according to the teachings of the present invention with an explosive apparatus, such as explosive apparatus 60. In the embodiment illustrated, the function of such a coupling means is performed by an extension of casing 12 of bioremediation apparatus 10 and an extension of shell 62 of explosive apparatus 60. Alternatively configured structures can, however, perform the function of such a coupling means.

For example, a wedge fit can be effected between bioremediation apparatus 10 and explosive apparatus 60 using respective angled male and female parts attached, respectively, to each. While the coupling means is primarily a mechanism to join bioremediation apparatus 10 and explosive apparatus 60, it is within the teachings of the present invention to provide structures that prevent bioremediation apparatus 10 and explosive apparatus 60 from being unintentionally separated, thereby performing the function of a locking means for securing bioremediation apparatus 10 and explosive apparatus 60 against the disengagement of the coupling together thereof.

Explosive apparatus 60 further comprises a capwell 72 positioned in open end 64 to receive detonators 74. Detonators 74 are in turn electrically connected by wires 76 to the exterior of shell 62 through wire access openings 78 shown in FIG. 2. A bioremediation portal 80 formed through capwell 72 communicates with explosive material 66 to afford access by mobilized microorganisms 30 from bioremediation outlet 42 to explosive material 66. A portal member 82 extends upwardly as shown in FIG. 3 from the center of capwell 72, encircling and defining on the interior thereof bioremediation portal 80. A portal O-ring 84 encircles portal member 82 to provide a fluid seal between sleeve member 44 and portal member 82 when explosive bioremediation apparatus 10 is coupled with explosive apparatus 60.

Figure 4:
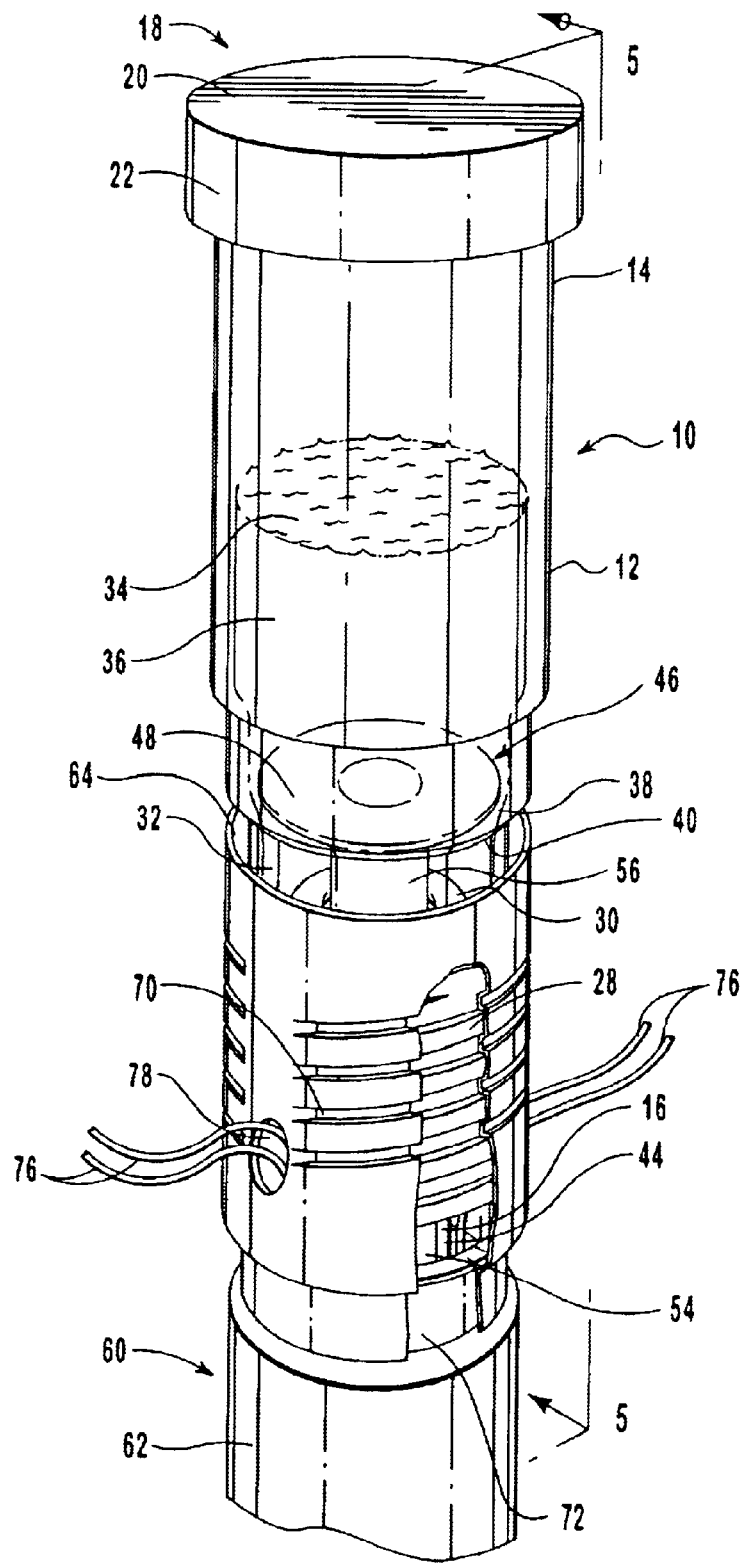
FIG. 4 is a perspective view in partial break-away of the bioremediation apparatus and the explosive apparatus of FIG. 2 immediately upon becoming fully coupled.
Figure 5:
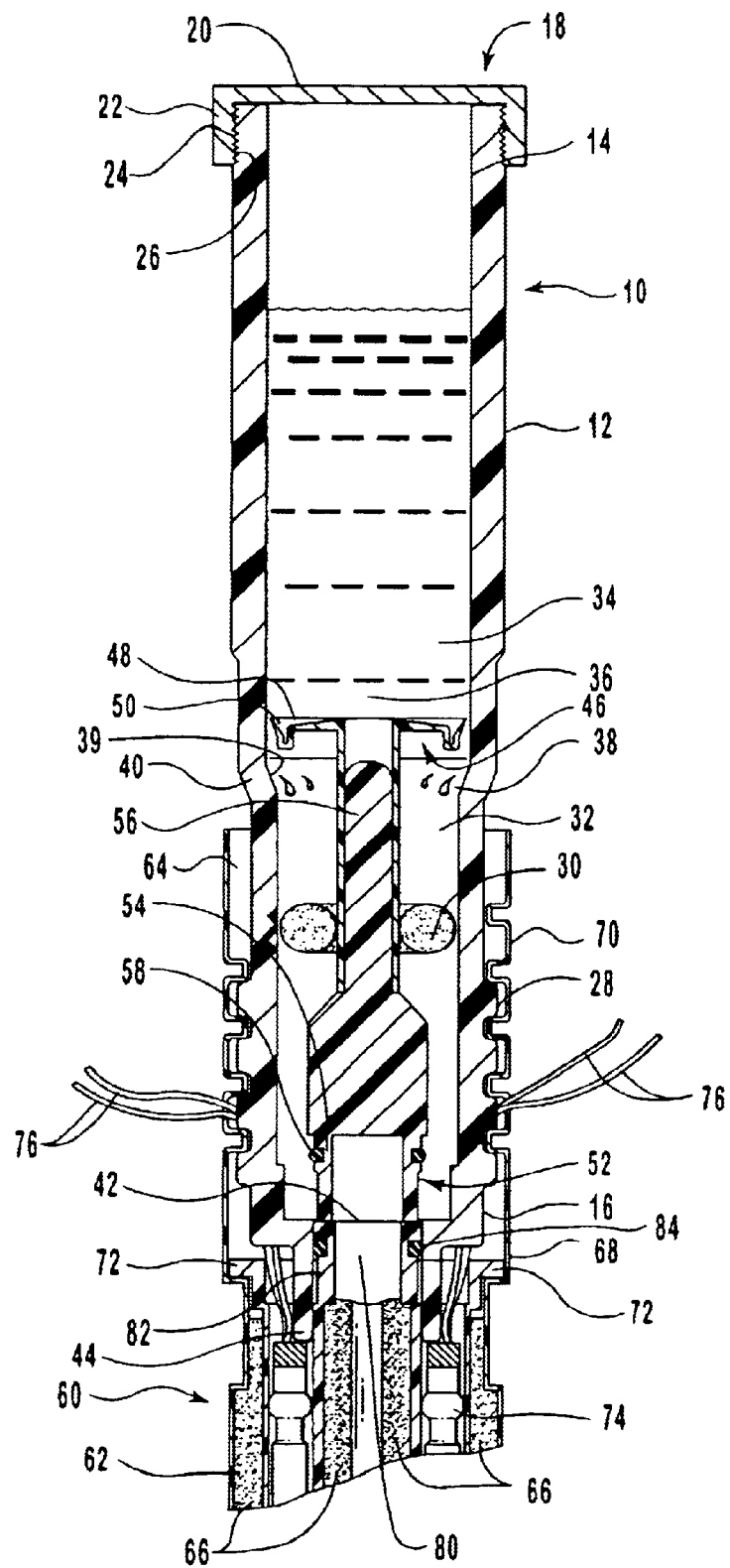
FIG. 5 is a cross-sectional elevation view of the bioremediation apparatus and the explosive apparatus illustrated in FIG. 4 taken along section line 5—5 shown therein.
Figure 6:
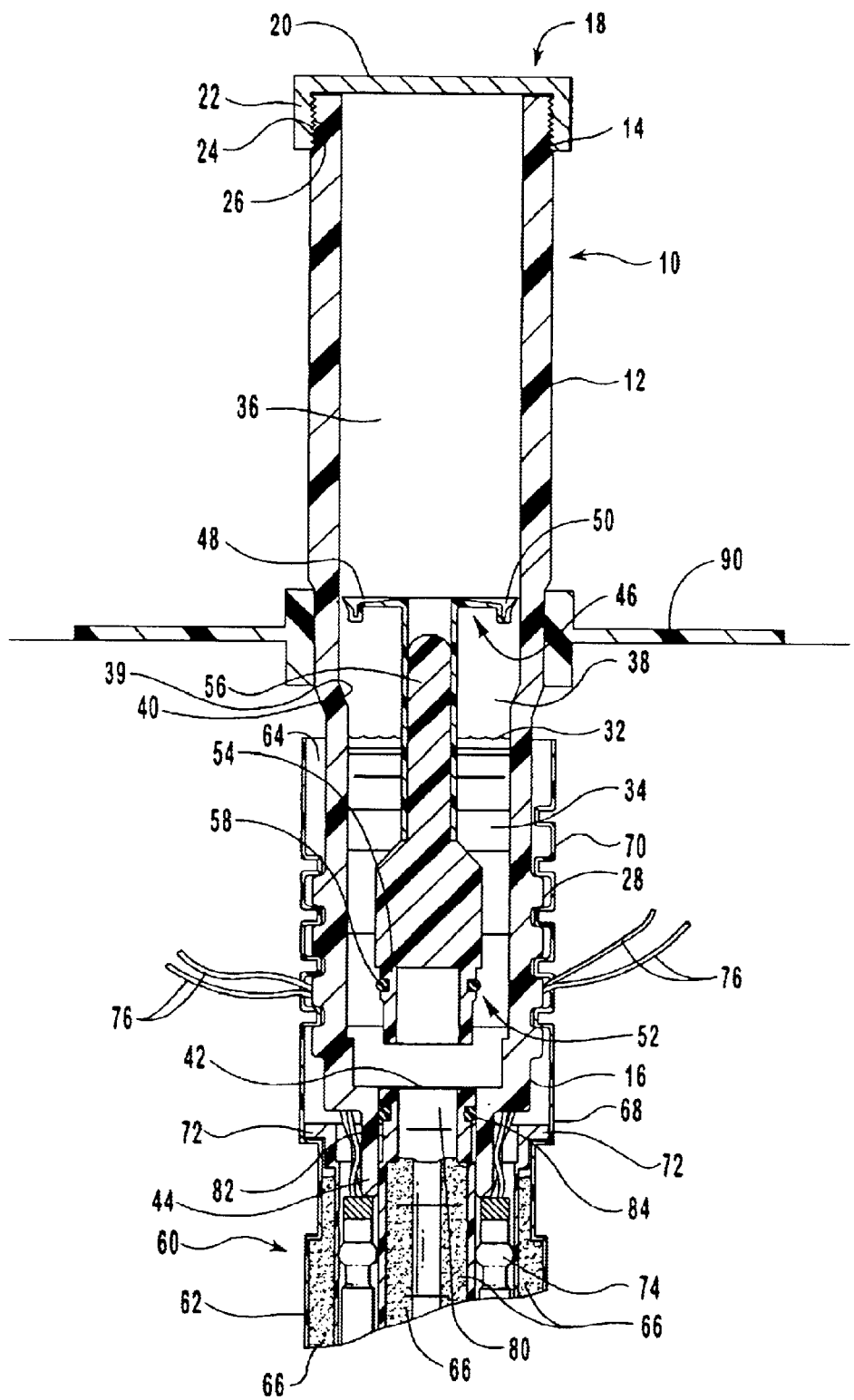
FIG. 6 is a cross-sectional elevation view like that of FIG. 5 illustrating the bioremediation apparatus and explosive apparatus in FIG. 4 at a time subsequent to that illustrated in FIG. 5 at which the explosive material in the explosive apparatus illustrated is contacted by hydrated microorganisms.

FIGS. 4 and 5 depict bioremediation apparatus 10 immediately after becoming completely coupled with explosive apparatus 60. FIG. 4 is a perspective view, and FIG. 5 is a cross-sectional view taken along section line 5—5 of FIG. 4. FIG. 5 illustrates to best advantage that as a result of the coupling of bioremediation apparatus 10 with explosive apparatus 60, first valve 46 and second valve 52 have been opened. Liquid 34 is shown being delivered by gravity from reservoir chamber 36 through liquid passage 38 to storage chamber 32.

As bioremediation apparatus 10 is being coupled with explosive apparatus 60, sleeve member 44 and portal member 82 advance toward each other until portal member 82 is positioned within sleeve member 44. A fluid seal is formed between sleeve member 44 and portal member 82 by portal O-ring 84. The advancement of bioremediation apparatus 10 brings portal member 82 into abutment against second valve member 54. As valve connector 56 effects a rigid interconnected relationship between second valve member 54 and first valve member 48, further advancement of bioremediation apparatus 10 into and toward explosive apparatus 60 forces second valve member 54 out of bioremediation outlet 42 and forces first valve member 48 out of liquid passage 38.

Sleeve member 44, second valve member 54, and portal member 82 can have any lengths that enable first valve 46 and second valve 52 to be opened. In the embodiment shown in FIGS. 5 and 6, portal member 82 and second valve member 54 each have a length that is less than the length of sleeve member 44, and the length of portal member 82 is approximately equal to or greater than the length of second valve member 54.

Forcing second valve member 54 and first valve member 48 upward within casing 12 opens a flow path that permits mobilized microorganisms 30 to contact explosive material 66 through bioremediation portal 80 as shown in FIG. 6.

First valve member 48, second valve member 54, and valve connector 56 form a divider which is preferably formed at least partially from a lightweight material such as polyethylene. The divider in this manner preferably has a lower density than water. This enables the divider to float to the top of the suspension of microorganisms as shown in FIG. 6 after the liquid has flowed into contact with explosive material 66.

The divider formed by first valve member 48, second valve member 54, and valve connector 56 is an example of a divider means for releasing microorganisms to an explosive material according to the teachings of the present invention. In an alternative embodiment, the divider means can take the form of a valve means for delivering the mobilized microorganisms from a storage means to an explosive material in a storage chamber of an explosive apparatus. The microorganisms are in a moist condition or are in a sufficient quantity of liquid to be characterized as a suspension or dispersion. Such an alternative embodiment accordingly utilizes but a single chamber and a single valve.

Portal member 82 is an example of an actuation means for initiating contact between mobilized microorganisms and an explosive material by opening first valve 46 and second valve 52. In an alternative embodiment, portal member 82 has a length greater than sleeve member 44, thereby rendering unnecessary any second valve member extending within sleeve member 44 to align portal member 82 for contact with the second valve member. In an additional alternative embodiment, second valve 52 is configured similarly to first valve 46. In this additional alternative embodiment, second valve 52 has a valve member within bioremediation outlet 42 that does not extend downward, and there is no sleeve member to provide alignment for portal member 82 in contacting the valve member to actuate second valve 52. Any structure capable of initiating access by mobilized microorganisms 30 to explosive material 66 is within the scope of the actuation means of the present invention.

The actuation means and the coupling means are taken together exemplary of a contact means for initiating and maintaining contact between mobilized microorganisms and an explosive material.

The coupling of bioremediation apparatus 10 with explosive apparatus 60 forms a system for in situ bioremediating of an explosive material. The system can be lowered into or driven down a borehole by contacting cap 18 with a tamping pole. Additionally, an anchor member 90 shown only in FIG. 6 can be positioned about casing 12 to maintain the system in the upright position illustrated during installation of the system at the bottom of a borehole. Anchor member 90 is preferably a disc circumferentially encircling casing 12 and extending perpendicularly outwardly therefrom. The longitudinal position of anchor member 90 along the length of casing 12 is maintained as shown in FIG. 6 by the increase in the outer diameter of casing 12 above anchor member 90.

The failure of installed explosives to detonate is primarily caused by the forces experienced during positioning of the system in the bottom of a borehole. In the process, wires 76 are often broken or disconnected from detonators 74, so that detonation cannot occur. When this happens, the digestion of explosive material 66 by microorganisms 30 will proceed in due course. Eventually, explosive material 66 will be reduced to nonexplosive and non-harmful materials that are neither detonatable by any activities in the vicinity, nor are an environmental contaminant.

Over time, by exposing an undetonated charge to the microorganisms, the entirety of the explosive material of the charge is reduced to a substance that cannot be detonated. In the illustrated embodiments of the present invention, the digestive activity of microorganisms 30 disarms explosive material 66 by first attacking the area around the capwell end of the explosive apparatus. This is where detonation is actually initiated. There is, however, no overall detrimental effect on the ability of an explosive charge to be detonated immediately after being initially contacted by bioremediating microorganisms. The initial activity of the microorganisms in the vicinity of the capwell can prevent accidental detonation of the explosive charge which can be caused, for example, by digging in the area of the explosive charge after the explosive charge is positioned in a borehole.

The time period required for the microorganisms to first disable an explosive, and then to fully remediate a given quantity of intermediate chemical materials depends on the amount and type of explosive material used, as well as the composition of microorganism consortium used therewith. Depending on design, relative concentrations of the explosive, the time required can be days, weeks, months, or years.

FIGS. 7 and 8 depict a second embodiment of a system for in situ bioremediating of an explosive according to teachings of the present invention. The system shown there comprises a bioremediation apparatus 100 and an explosive apparatus 110. Components shown in FIGS. 7 and 8 that are identical to the components shown in FIGS. 1–6 are identified with the same reference characters as are the corresponding components in FIGS. 1–6.

Bioremediation apparatus 100 has a cap 18, a spacer 112, and an anchor member 90 that encircles top end 14 of casing 12. Cap 18 and a spacer 112 are configured to maintain anchor member 90 on a nib 114. Cap 18 has cap threads 24 which cooperate with end threads 26 around top end 14 of casing 12 to seal top end 14 of casing 12. Spacer 112 is positioned between cap 18 and anchor member 90. Spacer 112 has a bottom portion not shown in the figures that is positioned within the top end of anchor member 90. When the system of FIGS. 7 and 8 is pushed down a borehole with a tamping pole, anchor member 90 cannot be dislodged from nib 114, since anchor member 90 abuts spacer 112, and cap 18 retains spacer 112 in position.

Liquid 34 is contained in reservoir chamber 36 and is released to contact microorganism 30 in storage chamber 32 when a first valve 116 in liquid passage 38 is opened. First valve 116 comprises the interior of neck 40 and a first valve member 118. First valve member 118 has a lip end 120 around the perimeter of first valve member 118. Lip end 120 is tapered to correspond to the dimensions of the interior of neck 40 and is flexible, thereby to form a fluid seal with liquid passage 38.

A second valve 122 comprises a second valve member 124 and a lip seal member 126. Second valve member 124 is the tapered bottom end of a valve connector 128. Lip seal member 126 extends from sleeve member 44 into bioremediation outlet 42 to form a fluid seal with second valve member 124.

First valve member 118 is integrally formed with valve connector 128, and valve connector 128 is integral with second valve member 124. Accordingly, first valve member 118, valve connector 128, and second valve member 124 together form an integral divider. In the first embodiment shown in FIGS. 1–6, the first valve means is also connected to the second valve means, as first valve member 48 and second valve member 54 are connected by valve connector 56. Thus, both in the first embodiment of FIGS. 1–6 and in the second embodiment of FIGS. 1–8, at least a portion or a component of each valve means is connected to at least a portion or a component of the other valve means.

The coupling means for coupling a bioremediation apparatus with an explosive apparatus, such as the combination of casing threads 28 and shell threads 70 as shown in FIGS. 1–8, may further comprise a means for indicating the position of the valves. In the preferred embodiment, casing 12 preferably has a bump not shown in the figures that causes a clicking noise when portal member 82 contacts the second valve member after casing threads 28 and shell threads 70 are advanced over each other. The clicking noise informs a user that the bioremediation apparatus and the explosive apparatus are coupled.

In yet additional alternative embodiments of an apparatus similar to the apparatus depicted in FIGS. 1–6 or in FIGS. 7–8, the first or second valve means can be electronically controlled to remain closed until electronically activated. For instance, a battery can provide electricity to retain a valve in a closed position such that the valve opens when the battery is dead. Accordingly, the microorganisms are not mobilized until after a time period equal to or exceeding the life span of the battery. In such an embodiment it is unnecessary to couple a bioremediation apparatus and explosive apparatus together to mobilize the microorganisms so the microorganisms and explosives can be contained in a single housing.

An example of an embodiment that utilizes an electrical mechanism is shown in FIG. 9 which is similar to the embodiment shown in FIGS. 7–8. Bioremediation apparatus 140 shown in FIG. 9 has microorganisms 30 which are not in the doughnut configuration but are added as a block. A flange 142 extends from valve connector 56 and is above a piston 144. Piston 144 extends within a spring 146 from a solenoid 148. Solenoid 148 is electrically connected to a battery 150. Battery 150 applies power to the coil of solenoid 148 which pulls piston 144 into the coil of solenoid 148 and retains piston 144 against the force of spring 146 as long as power is being supplied to the coil of solenoid 148. When the battery is dead then piston 144 and spring 146 are released and push against flange 142 which causes first valve member 48 and second valve member 54 to be pushed upward, thereby opening first valve 46 and second valve 52. In this embodiment, it is not necessary for sleeve member 44, second valve member 124 or portal member 82 to have lengths that enable the valve members to be opened.

Other embodiments utilize mechanisms which are primarily chemical in nature such as a barrier formed from a material, which is water soluble or slowly self-effacing in the presence of water, an aqueous solution or microorganisms. Thus, for example, self effacing barriers which eventually degrade and release the microorganisms can perform the functions of either or both first or second valve means according to the present invention. Examples of materials that can be utilized as self-effacing valve members include gelatin, alginate, starch, and acrylamide. Careful structural and material design of such barriers can produce relatively precisely timed releases. Alternatively, microorganisms encapsulated in a material such as gelatin or alginate may be releasably contained in a storage means of the present invention for eventual contact with an explosive material.

FIGS. 10–16 depict embodiments of the present invention wherein microorganisms are intermixed in the explosive or are disposed against an exterior surface of the explosive material. The microorganisms depicted in FIGS. 10–16 are disposed in sufficient proximity to said quantity of explosive material that the microorganisms can initiate bioremediation of the explosive material when the microorganisms are mobile. The explosive apparatus shown in FIGS. 10–16 do not require the coupling of a distinct bioremediation apparatus with a corresponding explosive apparatus.

Figure 10:
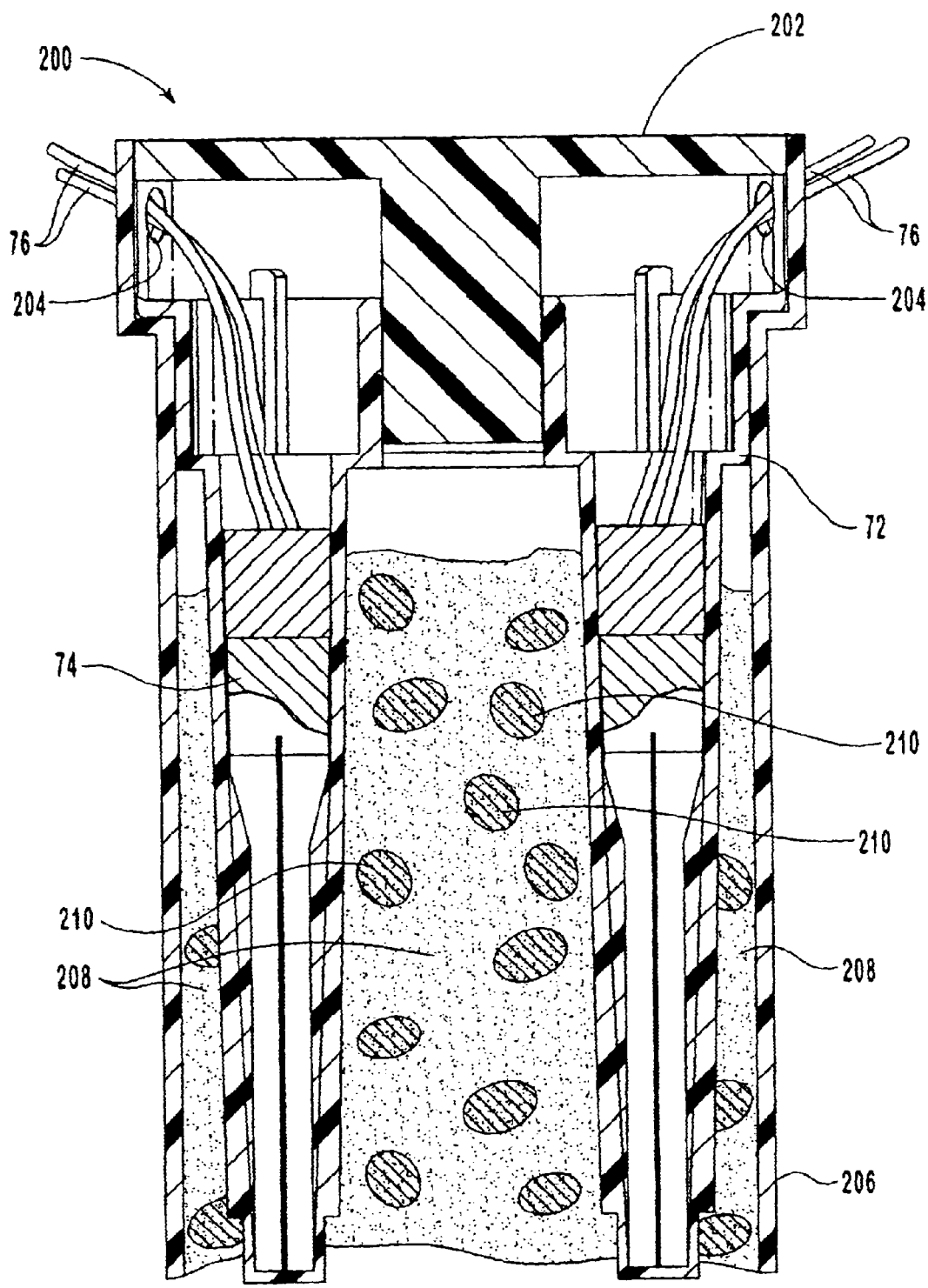
FIG. 10 is a cross-sectional elevation view of a fourth embodiment of an explosive apparatus comprising a pellet of microorganisms intermixed in the explosive material.
Figure 11:
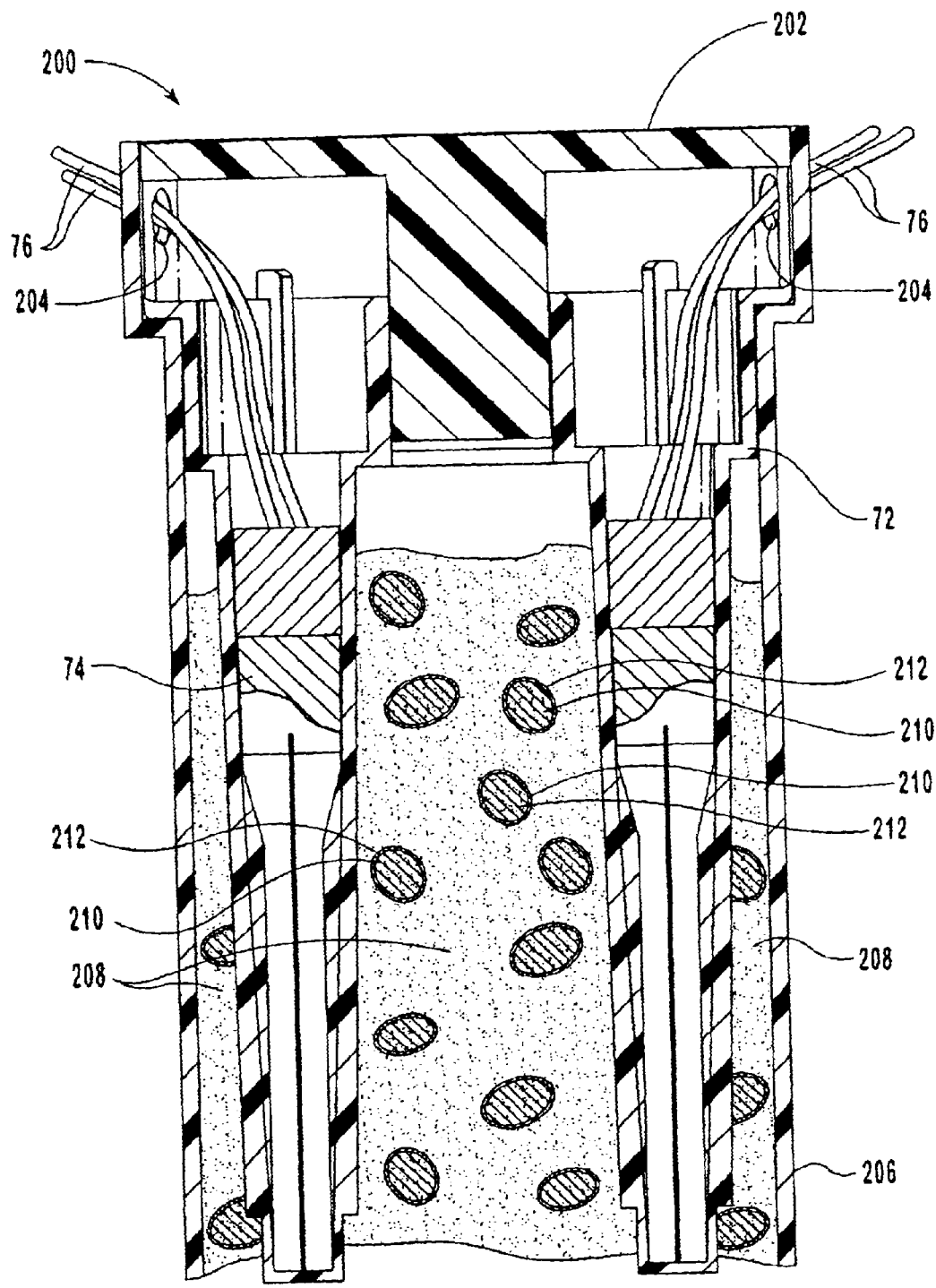
FIG. 11 is a partial cross-sectional elevation view of a fifth embodiment of an explosive apparatus which comprises an encapsulated pellet.
Figure 12:
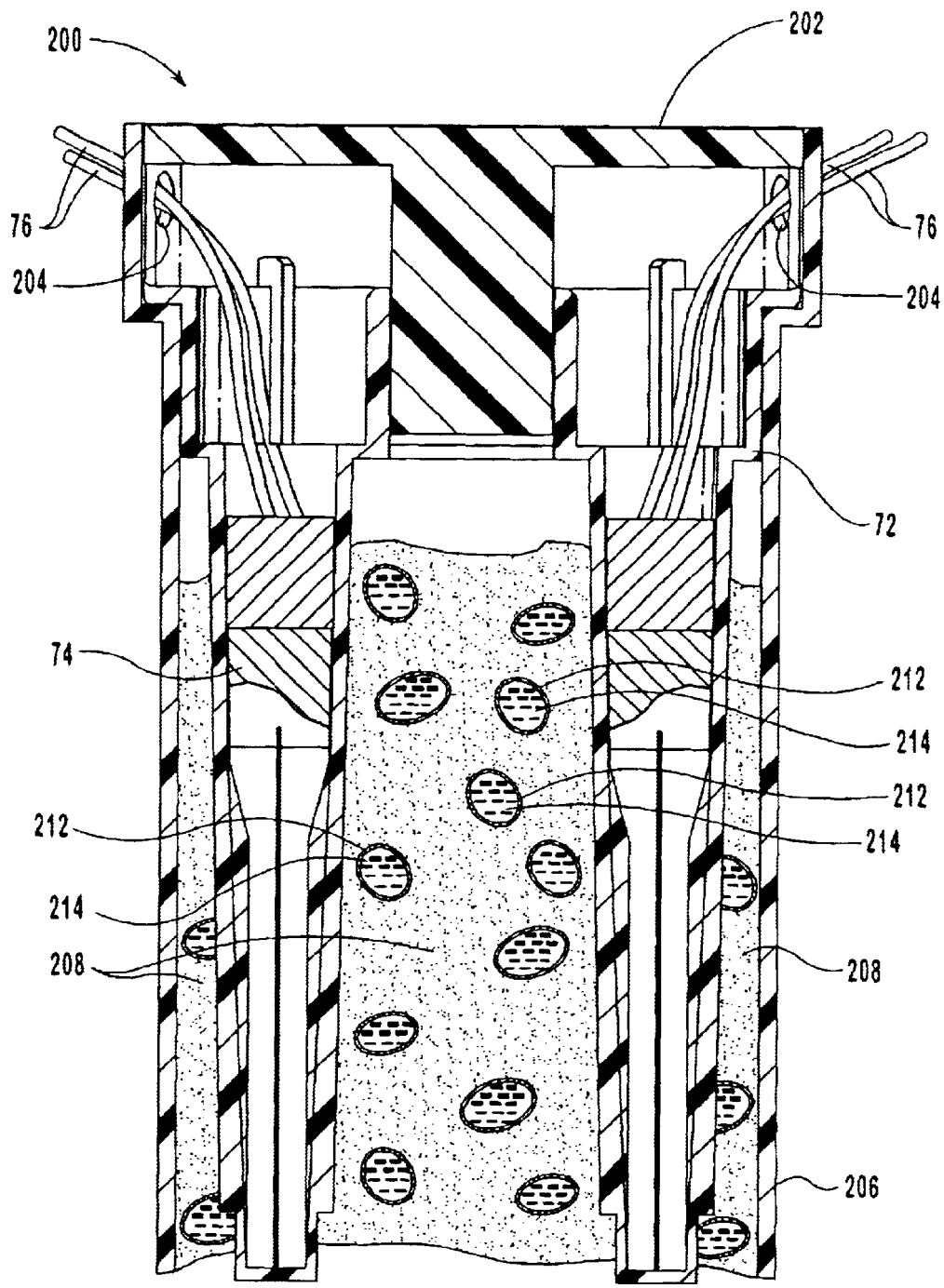
FIG. 12 is a partial cross-sectional elevation view of a sixth embodiment of an explosive apparatus which comprises an encapsulated suspension of microorganisms.
Figure 13:
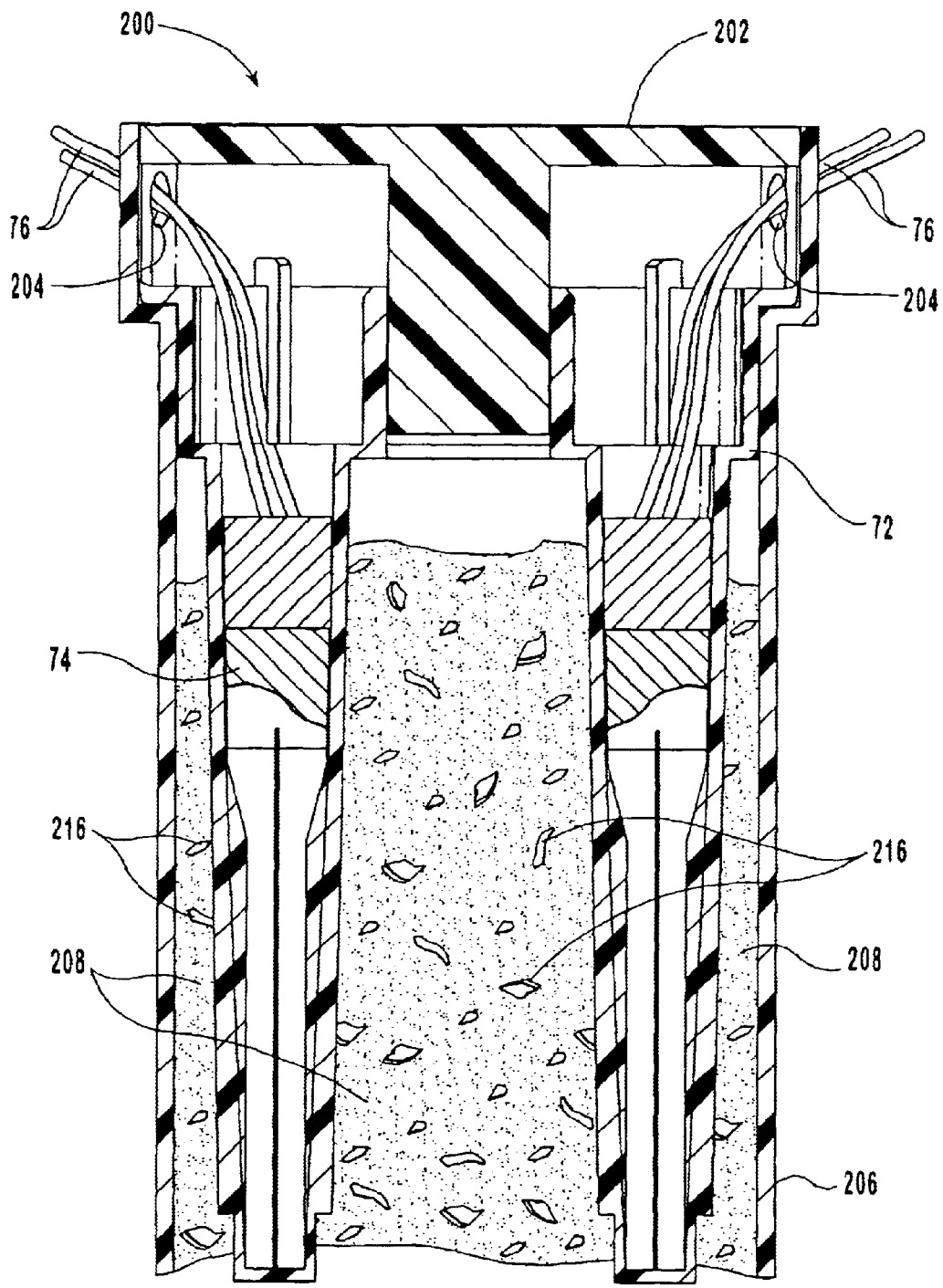
FIG. 13 is a partial factor that is closely related to the bioremediation rate of explosive materials by the microorganisms is the growth rate of the microorganisms. The growth rate of some species of microorganisms disclosed herein are logarithmic while others are only linear. Accordingly, the growth rate of the consortium depends on the type of microorganisms utilized. Additionally, the growth rate of the consortium of microorganisms depends on other factors, such as the availability of nutrients. The growth rate of the consortium of microorganisms can, however, be generally characterized as logarithmic.
Figure 14:
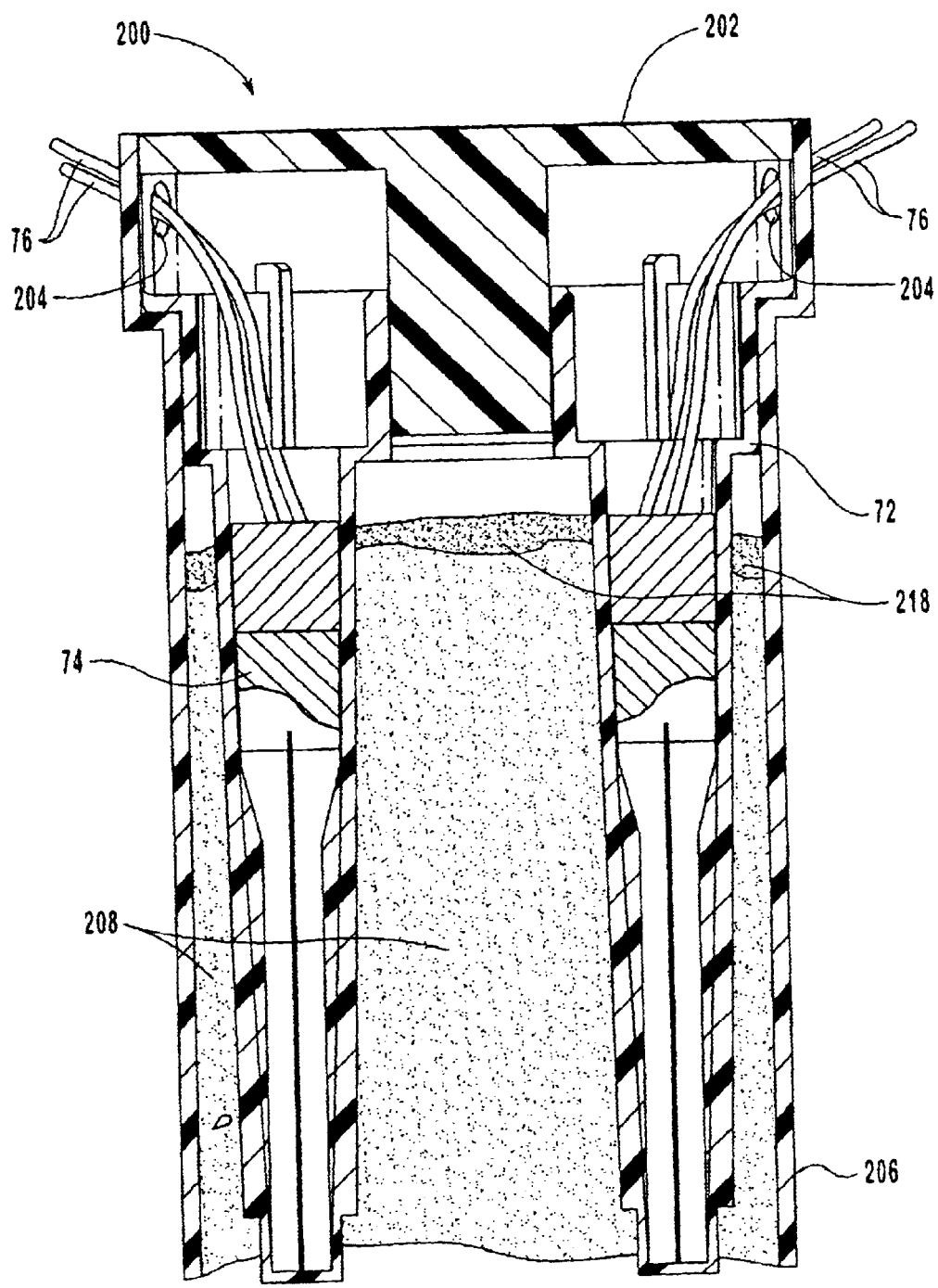
Figure 15:
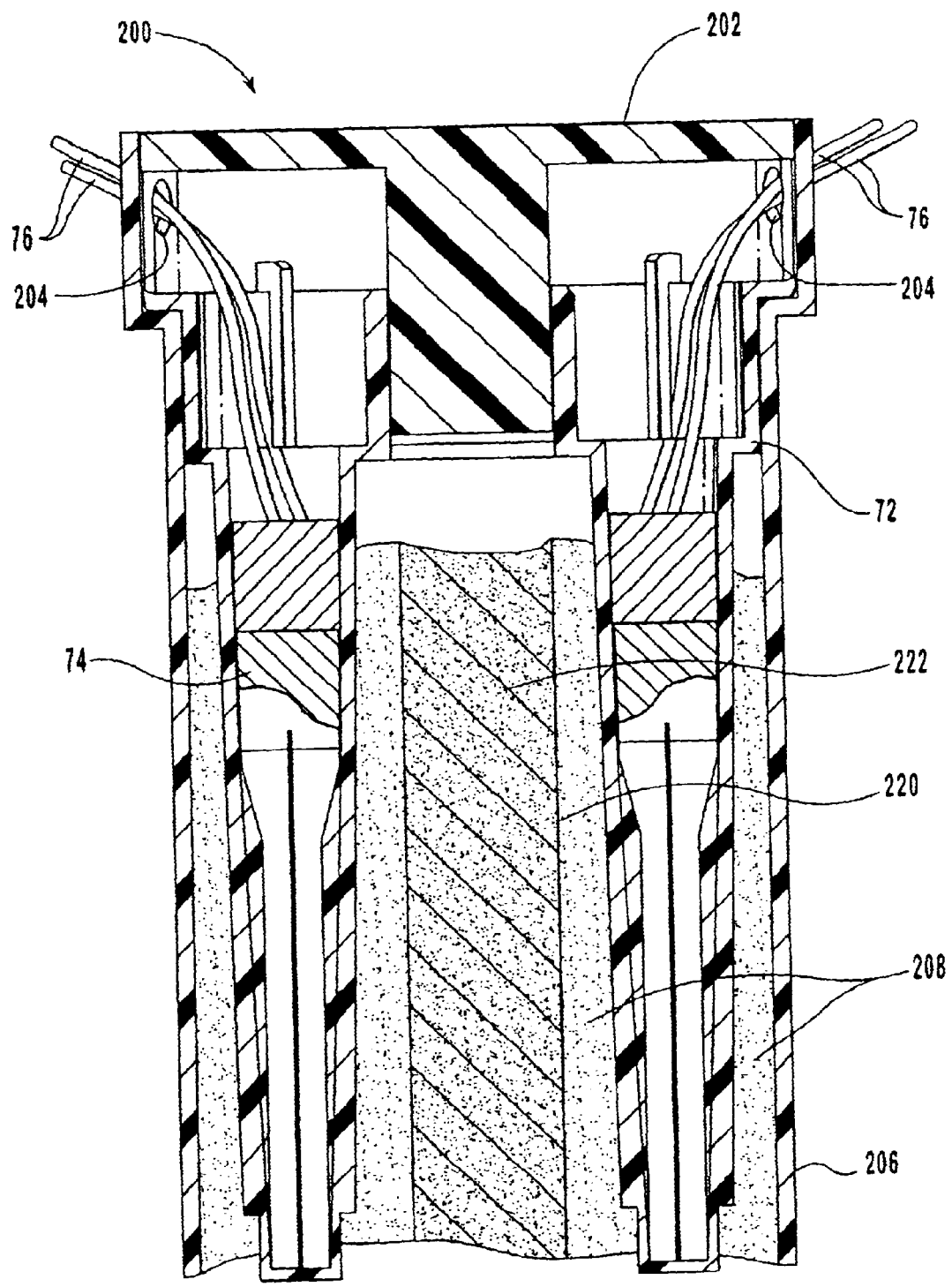
Figure 16:
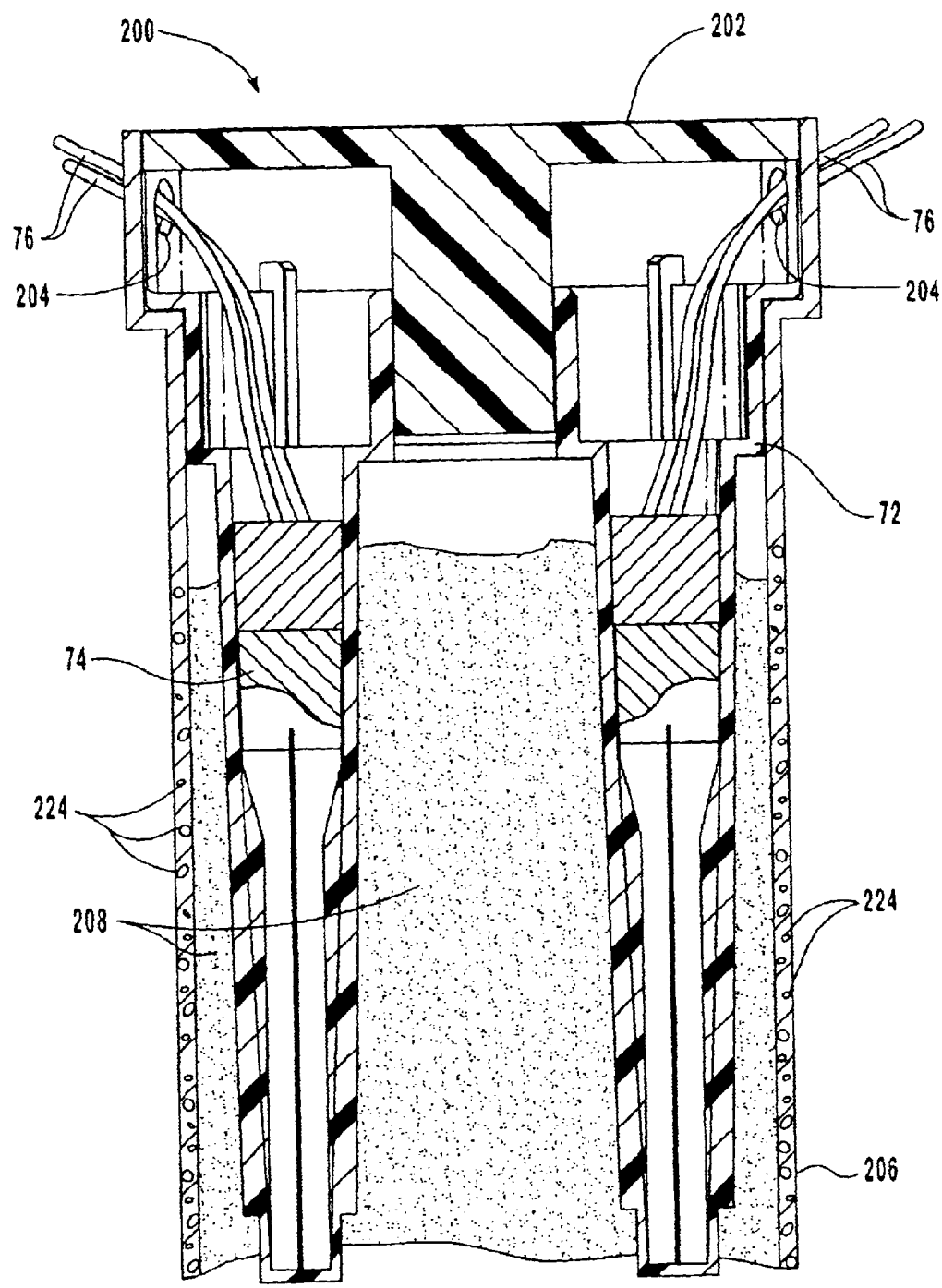

The microorganisms intermixed in the explosive material are generally in aggregations or clusters such as pellets as shown in FIG. 10, capsules as shown in FIGS. 11–12, or shards as shown in FIG. 13. The embodiments depicted in FIGS. 14–16 provide examples of microorganisms disposed against an exterior surface of the explosive material. FIG. 14 shows a powder of microorganisms dispersed on the top surface of the explosive material. FIG. 15 depicts microorganisms poured into a column within the explosive material. FIG. 16 depicts a cluster of microorganisms positioned within the shell that contains the microorganisms. In addition to the clusters or aggregations disclosed in FIGS. 10–16, the microorganisms can be positioned in any form even as individual microorganisms.

FIG. 10 illustrates an explosive apparatus 200 configured with an optional cap 202 and access openings 204 for wires 76. As in the embodiments depicted in FIGS. 1–9, explosive apparatus 200 has a capwell 72 with detonators 74. Explosive apparatus 200 further comprises a shell 206 containing an explosive material 208 and pellets 210 of microorganisms dispersed throughout explosive material 208. Shell 206 preferably enables water to flow through shell 206 to contact the explosive material 208 or at least into contact with the microorganisms in pellets 210 at the exterior surfaces of explosive material 208. Shell 206 may for example have an open end wherein water can flow, have holes or be water permeable to enable water to enter into the pores of explosive material 208.

Pellets 210 are dispersed as needed. For example, pellets 210 can be randomly dispersed, as shown, or concentrated as needed to deactivate the explosive charge. Pellets 210 are preferably positioned to facilitate desensitization of the explosive apparatus by being concentrated within explosive material 208 around detonators 74.

Pellets 210 can be positioned within explosive material 208 by any method and in any desired concentration. Control of the concentration and dispersion of pellets 210 in the explosive material 208 is maximized by adding pellets 210 to explosive material 208 when explosive material 208 is in a liquid state. Explosive material 208 is in a liquid state when being formed into a desired configuration by pouring the explosive material into a mold or directly into shell 206. The forming temperature of the explosive material is around 100° C. which is generally lethal to the microorganisms. Accordingly, the exposure time of microorganisms in pellets 210 to lethal temperatures is preferably minimized by adding pellets 210 to explosive material 208 while explosive material 208 is being formed or cast into a desired shape. Pellets 210 can also be pressed into explosive material 208 when explosive material 208 is solid or semi-solid at the time that the charge is manufactured.

The microorganisms or pellets 210 containing the microorganisms are preferably heat resistant to increase the survivability of the microorganisms when added to explosive material 208. There are several methods, which can be utilized alone or in combination, for obtaining heat resistant microorganisms or pellets.

One method for obtaining heat resistant microorganisms involves lyophilizing the microorganisms before the microorganisms are added to the hot explosive material. The microorganisms can be dehydrated by allowing the water to evaporate or preferably by freeze drying the microorganisms. Freeze drying the microorganisms dramatically reduces the mortality of the microorganisms due to thermal stress from exposure to the molten explosive material during the pouring process. It is speculated that freeze dried microorganisms are less susceptible to the lethal temperature effects than a microorganisms in a moist environment because the water content in the moist microorganism provides better heat transfer to the vital and temperature sensitive internal structures. The water removed from the freeze dried microorganisms is replaced at a later time in sufficient quantity to activate and mobilize the microorganisms.

The survivability of the microorganisms to thermal stress is also increased by increasing the thickness of the pellets 210. Increasing the thickness of pellets 210 decreases the rate of heat transfer to the interior of pellets 210, thereby protecting the microorganisms in the interior to the extent that the residence time of the microorganisms in the hot melt is not excessive. When the exterior microorganisms are destroyed they act as a thermal insulator for the microorganisms within the interior. Suitable pellets generally have an average diameter of about 3 mm.

Another method for reducing the mortality of microorganisms due to thermal stress is achieved by adding the microorganisms and explosive material into a mold in thin layers. By adding the microorganisms and explosive material incrementally in thin layers the layers can quickly cool thereby minimizing the exposure time of the microorganisms to the hot melt.

The heat resistance can also be increased by slowly raising the growth temperature of the microorganisms. By slowly raising the temperature of the environment of the microorganisms over a period of time during their growth, the high temperature tolerance of the microorganisms is significantly increased. Microorganisms can be utilized which have been adaptively developed or which have also been genetically developed. The microorganisms are preferably developed to have a very high survivability rate even when exposed to temperatures as high as about 100° C. Even microorganisms which have not been adequately developed to survive exposure to temperatures as high as about 100° C. are very useful since the temperature decreases as it is transferred into the pellet, yielding a greater interior portion that survive compared to a pellet utilizing unconditioned microorganisms. Accordingly, all microorganisms that have been developed for high temperature tolerance are useful and yield a higher survivability rate.

Additionally, pellets 210 can also be formed from mixtures of microorganisms and thermal protection additives that increase the heat resistance of the microorganisms. Examples of additives which have been found to increase the survivability of microorganisms when thermally stressed include dry milk and bentonite clay. These viability enhancers also can be used as binders as they tend to bind the constituents in the pellet together and can also be a nutrient source for the microorganisms. Insulative aggregates with no binding capability or that are not nutrient sources can also be used to thermally protect the microorganisms.

The pellets can be formed by compressing the microorganisms together along with any other constituent materials such as nutrients, binders and insulative materials. As previously set forth, the same component can act as a nutrient, binder or an insulative material. Nutrients are generally necessary even when the microorganisms are lyophilized since they provide the microorganisms with all of the materials needed for the microorganisms to fully grow and multiply. The explosives generally provide carbon and nitrogen while the nutrients generally provide phosphate and other chemicals. Any suitable nutrient can be utilized; however, depending on the type of nutrient utilized and the availability of the nutrient the growth rate can be influenced. In addition to the nutrients previously discussed such as starch, flour, bran, and milk; other suitable nutrients include milk sugar and minimal medium glycerol. Many of these nutrients can also act as stabilizers, such as starch, flour, bran, milk, glycerol in addition to phosphate buffered saline.

It is not always necessary to add a component that acts only as a binder since many nutrients can be utilized as a binder which are then converted into nutrients when contacted by a sufficient quantity of water to solubilize the binder. In addition to the binders previously mentioned, any suitable binder can be utilized. The binder is preferably an inorganic binder. A product sold as Diatab is a particularly useful binder or tablet base. Other materials that can be utilized as a binder include acrylamide, alginic acid or alginate, ethylcellulose, guar gum and gelatin.

Pellets 210 can also be encapsulated in a capsule 212 as shown in FIG. 11. The microorganisms in capsule 212 can be freeze dried, then formed into a pellet and encapsulated or the capsule can be formed by encapsulating moist microorganisms or a suspension of microorganism by pouring the suspension into a capsule and then drying or freeze drying the capsule. Any suitable materials for forming capsule 212 can be utilized. Examples of suitable materials include gelatin, starch, alginate and acrylamide.

While it is preferred to form the explosive by placing pellets of dehydrated microorganisms into molten explosive material since the molten explosive material is easily and relatively quickly molded into a desired shape, it can decrease the viability of the microorganisms. Accordingly, it is also desirable to form pellets 210 from moist microorganisms. Depending on the amount of liquid present, it may be necessary to introduce the microorganisms into explosive material 208 as a suspension of microorganisms as shown at 214 in FIG. 12 that is contained in a capsule 212. Microorganisms which are merely moist can also be encapsulated or can be introduced as shards 216 of a moist nutrient wafer containing microorganisms as shown in FIG. 13. Shards 216, which are fragments or flakes, can also be a nutrient wafer containing lyophilized microorganisms.

Clusters or aggregations of moist microorganisms in configurations such as pellets, capsules, shards, flakes and the like are preferably blended into explosive material 208 and then pressed into a mold. Moist microorganism clusters can also be pressed into explosive material 208. When the microorganisms are in a moist state but are blocked from contact with the explosive material or are not sufficiently. mobile, nutrients provide a minimal food source until the microorganisms can metabolize the explosive material. After the mixture is shaped into an explosive charge and the microorganisms are sufficiently moist it will bioremediate automatically within a predetermined time following manufacture.

An explosive apparatus is often left underground for periods of time up to six months and even up to a year. Accordingly, an explosive apparatus is preferably explodable for up to about six months and more preferably for up to about a year.

As previously set forth, the microorganisms can be concentrated around detonators 74 to desensitize the explosive since detonators 74 are typically more sensitive to impact and friction than explosive material 208. The time required to desensitize explosive apparatus 200 by disabling explosive material 208 around detonators 74 is dependent on many variables in addition to the distribution of the microorganisms, the growth rate of the types of microorganisms utilized, the ratio of microorganisms to explosives, the availability of particular nutrients, the types of microorganisms and explosives utilized and other physical condition such as pH, water availability and temperature. These same variables generally determine the time required to reduce explosive material 208 to a residual or negligible amount and the time required to entirely reduce explosive material 208 to a nonhazardous and preferably nonharmful material. Some of these additional variables include the amount of surface area exposed to the microorganisms, the mobility of the microorganisms, and the porosity of the explosive materials. Accordingly, the bioremediation rate can be designed as needed.

The porosity of the explosive materials is an example of a mobilization means for mobilizing the microorganisms to contact explosive material 208. The porosity of the explosive materials 30 enables the mobilized microorganisms to move within explosive material 208 and continue bioremediating explosive material 208. The porosity also enables water to enter into the pores and come into contact with the microorganisms and mobilize the microorganisms. A surfactant in explosive material 208 is another example of a mobilization means. Surfactants facilitate wetting of the crystals in explosive material 208 which enhances the mobility of the microorganisms and the accessibility of the crystals to the microorganisms.

Explosive apparatus 200 can be immersed in water before being placed in a borehole to allow water to pass through shell 206 and enter into the pores to mobilize the microorganisms or clusters thereof intermixed in explosive material 208. Explosive apparatus 200 is preferably exposed to a vacuum before being dipped in water. It is generally not necessary to immerse explosive apparatus 200 in water as groundwater is almost always present in the borehole. Additionally, water can also be poured into the borehole as needed. Water around or in contact with explosive apparatus 200 are additional examples of mobilization means for mobilizing the microorganisms.

Since groundwater is almost always in a borehole, it is generally desirable to design the explosive apparatus to utilize the groundwater. Accordingly, the porosity is preferably conducive to optimal capillary action through a network of microchannels. The network of microchannels or pores is sufficiently interconnected to provide optimal accessibility to the microorganisms by water and to provide optimal mobility to the mobilized microorganisms. The porosity is also designed to provide optimal surface area for the microorganisms to bioremediate. The porosity is balanced against the amount of explosive material that is preferably present and any necessary amount of mechanical strength for withstanding crushing and other forces experienced while being positioned in the borehole. The porosity can also be heterogenous throughout explosive material 208 such that the area around detonators 74 is more porous compared to other sections to expose more surface area.

The embodiments depicted in FIGS. 10–13 are dependent primarily on the porosity of explosive material 208 to provide access to the microorganisms and to provide mobilization pathways for the mobilized microorganisms. FIGS. 14–15 depict embodiments of the present invention that do not rely primarily on the porosity of explosive material 208.

FIG. 14 depicts microorganisms deposited as granules 218 on top of explosive material 208. Accordingly, as water passes through shell 206 the initial bioremediation activity of all of the microorganisms is concentrated at the portion of explosive material around detonators 74.

FIG. 15 depicts a chamber 220 centrally and longitudinally located within explosive material 208 that contains a suspension 222 of microorganisms. Microorganisms can also be positioned in chamber 220 which are merely moist or have been lyophilized. This configuration enables the mobilized microorganisms to bioremediate explosive material 208 from within a particular location in explosive material. The position of chamber 220 provides for controlled bioremediation of explosive material 208 around detonators 74.

FIG. 16 depicts another embodiment wherein shell 62 contains clumps 224 of microorganisms. Shell 62 is preferably formed from a material that is not only water permeable but also sufficiently water soluble to release the microorganisms contained in the shell. Examples of suitable materials include but are not limited to paper and polyvinyl alcohol. The microorganisms can then bioremediate explosive material 208 by beginning at the exterior of explosive material 208.

Yet another method of bioremediating explosives involves installing an explosive charge in a detonation site, such as a borehole, and then positioning microorganisms around the explosive charge by depositing microorganisms directly on the explosive charge and the detonation site. Similarly, a solution of microorganisms can be deposited at a detonation site. Then the explosive charge is placed in the suspension of microorganisms. Additionally, an explosive apparatus can be sprayed with or soaked in a suspension of microorganisms before being installed at a given detonation site, preferably while being exposed to a vacuum.

Experiments were conducted to study the process of remediating explosive materials according to the teachings of the present invention. To do so, a microorganism consortium was derived from soil and water samples obtained on the property of an established explosive manufacturer located at 8305 South Highway 6, Spanish Fork, Utah 84660 U.S.A. The microorganism consortium in the form of a suspension was combined with various types of explosive materials, either in solid form or in an aqueous suspension, and the results were observed and documented. The results of several of these tests are set forth below as examples.

EXAMPLE 1

Quantities of the explosive materials TNT and PETN in water were combined with the suspension of the microorganism consortium. The resulting mixture initially included 47.23 ppm of PETN and 40.63 PPM of TNT. The mixture was divided among containers that were stored in aerobic conditions at ambient temperature for various time periods. Table 1 below indicates the explosive analysis of these samples after each designated time interval. The explosive materials were substantially degraded after a period of five weeks.

TABLE 1

Aerobic Bioremediation of TNT and PETN

| Explosive Material | Initial Analysis | Analysis After 3 Days | Analysis After 5 Weeks |
|---|---|---|---|
| PETN | 47.23 ppm | 40.94 ppm | 7.25 ppm |
| TNT | 40.63 ppm | 5.32 ppm | 0.62 ppm |

EXAMPLE 2

The mixture prepared in Example 1 was stored in anaerobic conditions at ambient temperature and observed. The results were determined by HPLC analysis in ppm and averaged. Table 2 below sets forth the results obtained. As can be seen by comparing the results in Table 2 with the results in Table 1, the explosive materials tested remediated more rapidly under anaerobic conditions than under aerobic conditions.

TABLE 2

Anaerobic Bioremediation of PETN and TNT

| Explosive Material | Initial Analysis | Analysis after 3 Days | Analysis after 1 Week | Analysis after 5 Weeks |
|---|---|---|---|---|
| PETN | 47.23 ppm | 28.31 ppm | 24.46 ppm | 0.82 ppm |
| TNT | 40.63 ppm | 0.31 ppm avg. | 0.31 ppm avg. | None |

EXAMPLE 3

Discs of the explosive material Pentolite having a diameter of a pencil were split in two. When the discs were split each weighed about 0.1 gram. The discs were placed either in water as a control or in 6 ml to 8 ml of a suspension of the microorganism consortium. After a specific amount of time in aerobic conditions, the discs were dried and weighed or analyzed by HPLC. The liquid portions were analyzed by HPLC. The net remediated weight loss in the explosive material was determined by subtracting the control weight loss as a percentage from the weight loss as a percentage in each remediated explosive. The explosive loss by degradation is listed in Table 3 for each of the samples. The samples in B and C were tested for longer periods of time than the sample in A. The results of the testing of samples B and C show that significant bioremediation did not occur beyond the level achieved in sample A. This was most likely due to insufficient quantities of nutrients in samples B and C as the bioremediation activity probably ceased when the nutrients were consumed.

TABLE 3

Aerobic Bioremediation of Pentolite

| Sample No. | Sample or Test | Time | Initial Weight | Final dry weight plus weight of explosive in liquid portion. | Net Remediated Weight Loss |
|---|---|---|---|---|---|
| A | Control | 22 days | 0.1355 g | 0.1266 g = 6.57% loss | 6.97% Net Loss |
|   | Test | 22 days | 0.0981 g | 0.0848 g = 13.54% loss |   |

TABLE 3-continued

Aerobic Bioremediation of Pentolite

| Sample No. | Sample or Test | Time | Initial Weight | Final dry weight plus weight of explosive in liquid portion. | Net Remediated Weight Loss |
|---|---|---|---|---|---|
| B | Control | 88 days | 0.0578 g | 0.0557 g = 3.63% loss | 5.52% Net Explosive Loss |
|   | Test | 88 days | 0.0743 g | 0.0675 g = 9.15% loss |  |
| C | Control | 173 days | 0.1236 g | 0.1236 g = no loss | 6.78% Net Explosive Loss |
|   | Test | 173 days | 0.0737 g | 0.0687 g = 6.78% loss |  |

EXAMPLE 4

Experiments were conducted to compare remediation rates under aerobic and anaerobic conditions. Separate 5 gram samples of PETN/TNT Pentolite in a ratio of 60:40 were analyzed and placed in 100 ml to 300 ml suspension of a microorganism consortium. One was subjected to aerobic conditions; the other was subjected to anaerobic conditions. After various periods of time the samples were removed, air dried, and weighed to determine the amount of explosive material that had not degraded. The weight of the remaining explosive material was subtracted from the original weight to determine the weight of the explosive material lost due to bioremediation. The results are listed in Table 4 below. The results indicate that an insufficient amount of microorganisms were utilized or that the amount of nutrient was insufficient particularly in light of the results obtained in the other examples.

TABLE 4

Aerobic and Anaerobic Bioremediation of Pentolite

| Condition: Aerobic or Anaerobic | Original Weight | Time | Percent Wt Loss at Time listed | Time | Percent Wt Loss at Time Listed |
|---|---|---|---|---|---|
| Aerobic | 5.015 g | 66 days | 3.21% | 163 days | 5.43% |
| Anaerobic | 6.9027 g | — | — | 179 days | 3.10% |

EXAMPLE 5

Also investigated was the remediation according to the present invention of low levels of explosive materials in water. The explosive materials RDX and PETN were mixed with the water, combined with a suspension of a microorganism consortium, and then stored. The samples were tested by HPLC for explosive content initially and after 2 weeks. As shown in Table 5 below the bioremediation was nearly complete after two weeks.

TABLE 5

Bioremediation of Suspension of RDX and PETN

| Explosive Material | Initial Analysis | Analysis after 2 weeks |
|---|---|---|
| RDX | 6.6 ppm | Not detected |
| PETN | 25.0 ppm | Less than 0.5 ppm |

EXAMPLE 6

The remediation according to the present invention of soil contaminated with an explosive material was also investigated. Soil contaminated with the explosive material PETN was mixed with a suspension of a microorganism consortium and stored at ambient temperature. Samples were analyzed initially, after 44 days, and finally after 125 days. The PETN content in the soil dropped from 1659 ppm to 551 ppm. The results are set forth in Table 6 below.

TABLE 6

Bioremediation of Soil Contaminated with PETN

| Initial Analysis | Analysis after 44 Days | Analysis after 125 Days |
|---|---|---|
| 1659.2 ppm | 1193.2 ppm | 551.8 ppm |

EXAMPLE 7

In order to determine the effect of temperature on the growth of microorganism samples, the natural high temperature tolerances of the microorganism consortium were evaluated. The microorganism cultures were adapted to higher temperatures by slowly raising the growth temperature. By raising the temperature, the upper and lower limits of growth were both shifted upwards.

Two separate microbial growth stages were evaluated: the log phase, wherein the microorganisms experience logarithmic growth, and the stationary phase, wherein the microorganisms reach maximum growth. Microorganism cultures that enter the stationary phase late in their growth cycle induce the expression of genes which protect the microorganisms from various environmental stresses.

Four separate microorganism cultures were established. One culture, referred to as "30° C./Log Phase Culture", was comprised of new inocula, experiencing logarithmic growth, in fresh minimal medium, with TNT extract as the sole nitrogen source, and grown at 30° C. for three days. A second culture, referred to as "30° C./Stationary Phase Culture", was comprised of microorganisms that had reached maximum growth, in minimal medium, with TNT extract as the sole nitrogen source, previously grown at room temperature for several weeks, and additionally grown at 30° C. for three days. The third culture, referred to as "37° C./Log Phase Culture", was comprised of new inocula, experiencing logarithmic growth, in fresh minimal medium, with TNT extract as the sole nitrogen source, and grown at 37° C. for three days. The final culture, referred to as "37° C./Stationary Phase Culture", was comprised of microorganisms that had reached maximum growth, in minimal medium, with TNT extract as the sole nitrogen source, previously grown at room temperature for several weeks, and additionally grown at 37° C. for three days.

Samples of the four different microorganism cultures were subjected to temperatures ranging from 30° C. to 97° C. for twenty minutes. A small sample of each heated culture and a non-heated control culture were spread-plated on both nutrient agar plates, and minimal medium with 10% glycerol plates. The plates were incubated overnight at 30° C.

The microbial growth was evaluated according to the number of colony forming units of the plate or the visualization of distinct colonies. The results of this evaluation are illustrated in Table 7, below. Microbial growth covering the entire plate with few, if any, single colonies, was referred to as "total". Microbial growth greater than 1000 clearly defined colonies per plate, or too numerous to count, was referred to as ">1000". If the density of the sample was only slightly less than the density of the previous sample, an asterisk "*" appears after the notation. At the lower density levels, the colonies were distinguishable as comprising at least bacteria, "B" or fungus/filamentous bacteria, "F". The number preceding "B" or "F" corresponds to the number of distinct colonies.

TABLE 7

Temperature tolerance of microorganism consortium.

| Temp. ° C. | 30° C./Log Phase Culture | 30° C./Stationary Phase Culture | 37° C./Log Phase Culture | 37° C./Stationary Phase Culture |
|---|---|---|---|---|
| Control | Total | >1000 | Total | >1000 |
| 30° C. | Total | >1000 | Total | >1000 |
| 37° C. | Total | >1000 | Total | >1000 |
| 42° C. | Total | >1000* | Total | >1000 |
| 47° C. | Total* | >1000* | Total* | >1000 |
| 52° C. | 130 B | 180 F | Total* | 7 F |
| 57° C. | 0 colonies | 0 colonies | 0 colonies | 0 colonies |
| 62° C. | 0 colonies | 0 colonies | 0 colonies | 0 colonies |
| 67° C. | 0 colonies | 0 colonies | 2 colonies | 0 colonies |
| Control | Total | >1000 | Total | >1000 |
| 72° C. | 0 colonies | 0 colonies | 0 colonies | 0 colonies |
| 77° C. | 0 colonies | 0 colonies | 0 colonies | 0 colonies |
| 82° C. | 2 colonies | 0 colonies | 1 colony | 0 colonies |
| 87° C. | 0 colonies | 0 colonies | 0 colonies | 0 colonies |
| 92° C. | 0 colonies | 0 colonies | 0 colonies | 0 colonies |
| 97° C. | 0 colonies | 0 colonies | 0 colonies | 0 colonies |
| Control | Total | >1000 | Total | >1000 |

The log phase cultures appeared predominantly to contain a single colony type of microorganism. The stationary phase cultures contained a single microorganism colony type and an organism that appeared to be a fungus or a filamentous bacterium.

None of the heated culture samples exhibited significant growth beyond 57° C. The difference in the growth phase of the cultures, i.e., log phase versus stationary phase, did not result in a significant difference in growth. However, the 37° C./Log Phase Culture did appear to exhibit some growth advantage. Note that at 52°, the 37° C./Log Phase Culture still had microbial growth covering the entire plate, whereas the growth of the other samples had been reduced to countable quantities.

In addition, the 37° C./Stationary Phase Culture and 37° C./Log Phase Culture samples exhibited a growth advantage over the 30° C./Stationary Phase Culture and 30° C./Log Phase Culture which is commensurate with the differential initial growth temperature of these samples. That is, because microorganism cultures can be adapted to higher temperatures within limits by slowly raising or lowering the growth temperature, by raising the temperature, the upper and lower limits of growth are both shifted upwards. Thus the 37° samples were amenable to more substantial growth at higher temperatures than the 30° samples.

Along these lines, a new culture of the 37° C./Log Phase Culture was established using minimal medium with TNT. A sample of this culture was placed in a water bath wherein the temperature was raised 1° C. every two days. Significant growth was exhibited as high as 41° C.

EXAMPLE 8

In order to assess the survival characteristics of the microorganism culture during cooling of the explosive charge, the following simulated casting experiment was performed using the 37° C./Log Phase Culture. Small samples of this culture were placed in tubes in water baths at 95° C. and 80° C. These water baths were programmed to drop 1° C. every minute based on a reasonable approximation of the rate of cooling experienced by the charge. At five minute intervals, small samples were removed from the tubes in the water baths and plated on nutrient agar plates. These plates were incubated at 30° C. overnight and checked at 12 and 36 hours for microorganism colonies. After 36 hours the growth on the plates was evaluated. A non-heated sample was included as the control. The results of this study are illustrated in Table 8 below.

The results of this study indicate that the samples from the 80° C. water bath had a better survival rate than the samples from the 95° C. water bath.

TABLE 8

Temperature tolerance of microorganism consortium in simulated casting.

| Temperature | Time | 95° C. Bath | 80° C. Bath |
|---|---|---|---|
| Control | 0 min | Total | Total |
| 90° C. | 5 min | 0 colonies | NA |
| 85° C. | 10 min | 1 colony | NA |
| 80° C. | 15 min | 0 colonies | NA |
| 75° C. | 20 min/5 min | 0 colonies | 1 colony |
| 70° C. | 25 min/10 min | 1 colony | 2 colonies |
| 65° C. | 30 min/15 min | 1 colony | 1 colony |
| 60° C. | 35 min/20 min | 1 colony | 3 colonies |
| 55° C. | 40 min/25 min | 0 colonies | 1 colony |
| 50° C. | 45 min/30 min | 0 colonies | 4 colonies |
| 45° C. | NA/35 min | NA | 3 colonies |
| 40° C. | NA/40 min | NA | 1 colony |
| 35° C. | NA/45 min | NA | 5 colonies |

EXAMPLE 9

The purpose of the following evaluation was to demonstrate that any growth on TNT was greater than that which might be expected from low level contamination by nitrogen from other sources. In order to evaluate the growth characteristics of the microorganism culture with respect to the nitrogen supply, the following experiment was performed under aerobic conditions.

A sample of the 37° C./Log Phase Culture was placed in each of three fresh media formulations. The first contained mineral salts defined medium (MMO) and ammonia as the nitrogen source. The second contained MMO and TNT as the nitrogen source. The third contained only MMO and no added nitrogen. The cultures were then grown and shaken in an incubator at 37° C.

Growth was measured by evaluating the optical density of the culture. Samples removed from each culture were placed in a spectrophotometer and the optical density was measured at a wavelength of 425 nanometers, a wavelength not normally absorbed by molecules produced by the microorganisms. The optical density of the culture samples represents dispersion of the incident beam by the particulate microorganism. The higher the optical density value, the greater the amount of microbial growth. The optical density results are illustrated in Table 9, below.

TABLE 9

Effect of Nitrogen upon growth of microorganism consortium under aerobic conditions.

| Time | Optical Density of Culture in Ammonia Medium | Optical Density of Culture with TNT | Optical Density of Culture Absent Addition of Nitrogen |
|---|---|---|---|
| 0 hours | 0.006 | 0.166 | 0.005 |
| 20 hours | 0.008 | 0.152 | 0.018 |
| 48 Hours | 0.010 | 0.144 | 0.023 |
| 146 Hours | 1.520 | 0.432 | 0.073 |
| Difference | 1.514 | 0.266 | 0.068 |
| Over Background | NA | 3.99 | NA |

The TNT and No Nitrogen cultures were significantly less productive than the ammonia supplemented cultures. Still the TNT supplemented culture values were consistently higher than the No Nitrogen values. This indicates that the cultures were using TNT as the nitrogen source in the TNT supplemented culture.

EXAMPLE 10

Another study, similar to Example 9, above, was performed under anaerobic conditions. A sample of the 37° C./Log Phase Culture was placed in each of three fresh media formulations. The first contained mineral salts defined medium (MMO) and ammonia as the nitrogen source. The second contained MMO and TNT as the nitrogen source. The third contained only MMO and no added nitrogen. The cultures were placed in sealed serum bottles and the atmosphere was replaced with pure Nitrogen. Cultures were incubated without shaking in an incubator at 37° C. The results of this study are illustrated in Table 10, below.

TABLE 10

Effect of Nitrogen upon growth of microorganism consortium under anaerobic conditions.

| Time | Optical Density of Culture in Ammonia Medium | Optical Density of Culture with TNT | Optical Density of Culture Absent Additional Nitrogen |
|---|---|---|---|
| 0 hours | 0.008 | 0.204 | 0.005 |
| 20 hours | 0.012 | 0.218 | 0.009 |
| 48 Hours | 0.017 | 0.268 | 0.007 |
| 146 Hours | 0.482 | 0.272 | 0.019 |
| Difference | 0.474 | 0.068 | 0.014 |
| Over Background | NA | 4.88 | NA |

Once again, the TNT and No Nitrogen cultures were significantly less productive than the ammonia supplemented cultures. Still the TNT supplemented culture values were consistently higher than the No Nitrogen values. This indicates that the cultures were using TNT as the nitrogen source in the TNT supplemented culture. Overall, the anaerobic conditions showed less growth than the aerobic cultures.

EXAMPLE 11

In order to evaluate the thermal resistance of the microorganism consortium in a system which will adequately mimic those of a pentolite pour, fresh samples of a TNT grown consortium and a control absent TNT were freeze dried and tested directly for temperature sensitivity. The freeze dried samples were placed into aluminum foil packets. Aluminum foil was used because its heat transference properties ensured that the temperature experienced by the freezed dried powder approximated that produced by the oven. The foil packets were placed in an oven at a starting temperature of either 100° C. or 80° C. The initial 100° C. and 80° C. temperatures were maintained for 2 minutes. Each temperature was then incrementally decreased at the rate of 1° C. per minute to 35° C. The packets remained at 35° C. for 10 minutes and were then removed from the oven. The contents of the packets were placed in MMO with TNT and glycerol, and then placed in a shaking incubator at 37° C.

The negative controls were void of any color which indicates complete absence of nitrogen degradation. All other samples were in various stages of TNT degradation as indicated by the color reduction in the samples from colorless to light orange to deep red or violet. The samples that started at 80° C. exhibited more advanced TNT degradation than those that started at 100° C.

These results were in accordance with the results of Example, 8, above. To reiterate, in that study the samples from the 80° C. water bath had a more optimal survival rate that the samples from the 95° C. water bath. Therefore, although the consortium did respond after experiencing temperatures as high as 100° C., a maximum of 80° C. represented the more optimal initial temperature.

The lyophilized microorganisms still produced significant bioremediation results even after being exposed to temperatures corresponding to that of a hot melt of explosive material. Accordingly, it can be concluded that lyophilization of microorganisms dramatically improves the thermal resistance of the microorganisms.

EXAMPLE 12

In order to further evaluate the thermal tolerance and protection of the microorganism consortium, freeze drying was compared with microencapsulation. The microencapsulation procedure required maintaining a substantial amount of fresh cell culture. The cells were divided into 4 samples and resuspended in phosphate buffered saline (PBS); PBS and 3% dried milk; PBS and 3% bentonite clay; and minimal medium with glycerol. Samples of the four suspensions were prepared by freeze drying 2 ml portions. The remainder of the suspensions was divided into 2 samples for encapsulation into alginate and polyacrylamide. Encapsulation into alginate was accomplished by adding sodium alginate to the suspension sample and then adding the mixture dropwise into a Calcium Chloride solution, with a molarity of 0.1. Encapsulation into polyacrylamide was accomplished by combining a biacrylamide mixture with a catalyst, such as a product sold as Temed, and beta-mercaptoethanol. As the mixture polymerized, the microorganism suspension was trapped in a gel matrix. Half of each sample selected for encapsulation (alginate or polyacrylamide), was freeze dried and the other half was air dried.

All samples, (freeze dried, encapsulated and freeze dried, encapsulated and air dried), were exposed to the temperature curve of Example 8, above. The samples were then added to low temperature agar and overlaid on total nutrient agar. Outgrowth and survival of the samples was evaluated. Additional portions of each sample were then added back to minimal medium with glycerol and TNT to assess the survival of the TNT-critical portions of the consortium.

The encapsulated samples did not result in a significant difference in growth as compared with the freezed dried samples. Thus encapsulation did not offer any distinct advantage over freeze drying with respect to temperature tolerance and subsequent survivability of the microorganism consortium.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed is:

1. A method for manufacturing an explosive device capable of self-remediation, if the explosive device fails to detonate as intended, said method comprising the steps:
   (a) forming a quantity of an explosive material into an explosive device;
   (b) identifying microorganisms capable of bioremediating said explosive material; and
   (c) positioning a quantity of said microorganisms in such proximity to said quantity of said explosive material in said explosive device that, when said quantity of microorganisms is mobilized, said microorganisms in said quantity thereof are capable of bioremediating said quantity of said explosive material in said explosive device, whereby if said explosive device is installed at a detonation site and fails to detonate as intended, when said quantity of microorganisms is mobilized, said microorganisms in said quantity thereof deactivate said explosive device by bioremediating said quantity of said explosive material in situ at the detonation site.

2. A method as recited in claim 1, wherein said microorganisms are selected from a group of microorganisms consisting of Pseudomonas spp., Escherichia spp., Morganella spp., Rhodococcus spp., Comamonas spp., and denitrifying microorganisms.

3. A method as recited in claim 1, wherein said microorganisms are selected from a group of microorganisms in Pseudomonas spp. consisting of aeruginosa, fluorescens, acidovorans, mendocina, and cepacia.

4. A method for manufacturing an explosive device capable of self-remediation, if the explosive device fails to detonate as intended, said method comprising the steps:
   (a) forming a quantity of an explosive material into an explosive device;
   (b) identifying microorganisms capable of bioremediating said explosive material, said microorganisms being among a microorganism consortium identified at the American Type Culture Collection by ATCC Designation No. 55784; and
   (c) positioning a quantity of said microorganisms in such proximity to said quantity of said explosive material in said explosive device that, when said quantity of microorganisms is mobilized, said microorganisms in said quantity thereof are capable of bioremediating said quantity of said explosive material in said explosive device, and if said explosive device is installed at a detonation site and fails to detonate as intended, said microorganisms in said quantity thereof deactivate said explosive device by bioremediating said quantity of said explosive material in situ at said detonation site.

5. A method as recited in claim 1, wherein said explosive material is selected from a group of explosive materials consisting of organic nitroaromatic explosives, organic nitramine explosives, and organic nitric ester explosives.

6. A method as recited in claim 1, wherein said explosive material is selected from a group of explosive materials consisting of trinitrotoluene, hexanitrostilbene, hexanitroazobenzene, diaminotrinitrobenzene and triaminotrinitrobenzene, cyclotrimethylene trinitramine, cyclotetramethylene tetranitramine, nitroguanidine, 2,4,6-trinitrophenylmethylnitramine, pentaerythritol tetranitrate, nitroglycerine, and ethylene glycol dinitrate.

7. A method as recited in claim 1, wherein said microorganisms are sufficiently mobile to commence bioremediation of said explosive material.

8. A method as recited in claim 1, further comprising the step of providing mobilization means for mobilizing said microorganisms to contact said quantity of said explosive material.

9. A method for manufacturing an explosive device capable of self-remediation, if the explosive device fails to detonate as intended, said method comprising the steps:
   (a) forming a quantity of an explosive material into an explosive device;
   (b) identifying microorganisms capable of bioremediating said explosive material; and
   (c) positioning a quantity of said microorganisms in such proximity to said quantity of said explosive material in said explosive device that, when said quantity of microorganisms is mobilized, said microorganisms in said quantity thereof are capable of bioremediating said quantity of said explosive material in said explosive device, whereby if said explosive device is installed at a detonation site and fails to detonate as intended when said quantity of microorganisms is mobilized, said microorganisms in said quantity thereof deactivate said explosive device by bioremediating said quantity of said explosive material in situ at the detonation site, wherein said step of positioning comprises depositing said microorganisms in a structure having a removable barrier between said microorganisms and said quantity of said explosive material.

10. A method as recited in claim 9, wherein said barrier is removable mechanically.

11. method as recited in claim 9, wherein said barrier is removable electrically.

12. A method as recited in claim 9, wherein said barrier is removable chemically.

13. A method as recited in claim 1, wherein said step of positioning comprises the step of dispersing said microorganisms in said quantity of said explosive material.

14. A method as recited in claim 1, wherein said microorganisms are in an aggregation, and said method further comprises the step of shaping said aggregation into a form selected from the group consisting of a pellet, a capsule, a shard, a flake, a granule, a powder, and a clump.

15. A method as recited in claim 1, wherein said microorganisms are dehydrated.

16. A method as recited in claim 1, wherein said microorganisms are freeze dried.

17. A method as recited in claim 1, wherein said microorganisms are sufficiently resistant to heat that a significant portion of said microorganisms survive when said step of positioning occurs at a temperature of about 100° C.

18. A method as recited in claim 14, wherein said aggregation further comprises thermal protection additives.

19. A method as recited in claim 1, wherein said quantity of said explosive material is porous.

20. A method for manufacturing an explosive device capable of self-remediation, if the explosive device fails to detonate as intended, said method comprising the steps:
   (a) forming a quantity of an explosive material into an explosive device;
   (b) disposing said quantity of said explosive material in a shell, said shell enabling water from the exterior of said shell to flow through said shell into contact with said quantity of said explosive material;
   (c) identifying microorganisms capable of bioremediating said explosive material; and
   (d) positioning a quantity of said microorganisms in such proximity to said quantity of said explosive material in said explosive device that, when said quantity of microorganisms is mobilized, said microorganisms in said quantity thereof are capable of bioremediating said quantity of said explosive material in said explosive device, whereby if said explosive device is installed at a detonation site and fails to detonate as intended, when said quantity of microorganisms is mobilized, said microorganisms in said quantity thereof deactivate said explosive device by bioremediating said quantity of said explosive material in situ at the detonation site.

21. A method for manufacturing an explosive device capable of self-remediation, if the explosive device fails to detonate as intended, said method comprising the steps:
   (a) forming a quantity of an explosive material into an explosive device;
   (b) identifying microorganisms capable of bioremediating said explosive material;
   (c) shaping said microorganisms into aggregations having a form selected from the group consisting of a pellet, a capsule, a shard, a flake, a granule, a powder, and a clump; and
   (d) positioning said aggregations in such proximity to said quantity of said explosive material in said explosive device that, when said microorganisms in said aggregations are activated, said microorganisms in said aggregations are capable of bioremediating said quantity of said explosive material in said explosive device, whereby if said explosive device is installed at a detonation site and fails to detonate as intended, when said quantity of microorganisms is mobilized, said microorganisms in said quantity thereof deactivate said explosive device by bioremediating said quantity of said explosive material in situ at the detonation site.

22. A method as recited in claim 21, wherein said step of forming occurs before said step of positioning.

23. A method as recited in claim 22, wherein said step of positioning comprises the step of depositing said aggregations on an exposed surface of said explosive material in said explosive device.

24. A method for manufacturing an explosive device capable of self-remediation, if the explosive device fails to detonate as intended, said method comprising the steps:
   (a) forming a quantity of an explosive material into an explosive device, wherein said step of forming comprises disposing said quantity of said explosive material in a shell, and said shell enables water from the exterior of said shell to flow through said shell into contact with said quantity of said explosive material;
   (b) identifying microorganisms capable of bioremediating said explosive material;
   (c) shaping said microorganisms into aggregations having a form selected from the group consisting of a pellet, a capsule, a shard, a flake, a granule, a powder, and a clump; and
   (d) after said step of forming, positioning said aggregations in such proximity to said quantity of said explosive material in said explosive device that, when said microorganisms in said aggregations are activated, said microorganisms in said aggregations are capable of bioremediating said quantity of said explosive material in said explosive device, whereby if said explosive device is installed at a detonation site and fails to detonate as intended, when said quantity of microorganisms is mobilized, said microorganisms in said quantity thereof deactivate said explosive device by bioremediating said quantity of said explosive material in situ at the detonation site.

25. A method as recited in claim 24, wherein said step of positioning comprises the step of depositing said aggregations on a surface of said quantity of said explosive material in said shell.

26. A method as recited in claim 21, wherein said shell is porous, and said step of positioning comprises the step of embedding said aggregations in said shell.

27. A method as recited in claim 24, wherein said step of positioning comprises the step of inserting into said quantity of said explosive material in said shell a longitudinal core of said aggregations.

28. A method as recited in claim 21, wherein said explosive material in said explosive apparatus is porous.

29. A method as recited in claim 21, wherein a surfactant is mixed with said explosive material.

30. A method as recited in claim 21, wherein said step of positioning occurs before said step of forming.

31. A method as recited in claim 30, wherein said step of positioning comprises the step of dispersing said aggregations in said quantity of said explosive material.

32. A method as recited in claim 30, further comprising the step of introducing thermal protective additives into said aggregations.

33. A method for manufacturing an explosive device capable of self-remediation, if the explosive device fails to detonate as intended, said method comprising the steps:
   (a) forming a quantity of an explosive material into an explosive device;
   (b) disposing said quantity of said explosive material of said explosive device in a shell, said shell enabling water from the exterior of said shell to flow through said shell into contact with said quantity of said explosive material therein;
   (c) identifying microorganisms capable of bioremediating said explosive material;
   (d) housing.a quantity of said microorganisms in a bioremediation apparatus; and
   (e) coupling said bioremediation apparatus to said shell with said quantity of explosive material of said explosive device disposed therein, thereby positioning said quantity of microorganisms in such proximity to said quantity of said explosive material in said shell that, whereby when said quantity of microorganisms is mobilized, said microorganisms in said quantity thereof are capable of bioremediating said quantity of said explosive material in said explosive device, and if said explosive device is installed at a detonation site and fails to detonate as intended, said microorganisms in said quantity thereof deactivate said explosive device by bioremediating said quantity of said explosive material in situ at said detonation site.

34. A method as recited in claim 33, wherein said shell has an open end, a capwell positioned at said open end, and a bioremediation portal formed through said capwell communicating with said explosive material in said shell.

35. A method as recited in claim 33, wherein said bioremediation apparatus comprises:
  (a) storage means for releasably containing said microorganisms; and
  (b) divider means for selectively releasing said microorganisms from said storage means into contact with said explosive material in said explosive device.

36. A method as recited in claim 35, wherein said divider means comprises a removable barrier between said microorganisms and said quantity of said explosive material when said bioremediation apparatus is coupled to said explosive device.

37. A method as recited in claim 36, wherein said barrier is removable mechanically.

38. A method as recited in claim 36, wherein said barrier is removable electrically.

39. A method as recited in claim 36, wherein said barrier is removable chemically.

40. A method as recited in claim 35, wherein said bioremediation apparatus further comprises:
  (a) reservoir means for releasably containing a liquid capable of mobilizing said microorganisms; and
  (b) separation means for selectively releasing said liquid from said reservoir means into said storage means.

41. A method as recited in claim 33, wherein said bioremediation apparatus comprises:
  (a) reservoir means for releasably containing a liquid capable of mobilizing said microorganisms;
  (b) storage means for releasably containing said microorganisms, said storage means being in selective communication with said reservoir means;
  (c) first valve means for releasing said liquid from said reservoir means into said storage means in the open condition of said first valve means; and
  (d) second valve means for releasing said microorganisms and said liquid into contact with said explosive material in said explosive apparatus when said explosive apparatus is coupled to said explosive device.

42. A method as recited in claim 41, wherein said first valve means and said second valve means are operably interconnected.

43. A method for manufacturing an explosive device capable of self-remediation, if the explosive device fails to detonate as intended, said method comprising the steps:
  (a) selecting an explosive material from which to form an explosive device;
  (b) identifying microorganisms capable of bioremediating said explosive material;
  (c) dispersing a quantity of said microorganisms in a quantity of said explosive material, thereby forming an explosive mixture with bioremediating capacity; and
  (d) forming a quantity of said explosive mixture into an explosive device, whereby when said quantity of said microorganisms in said explosive mixture is mobilized, said microorganisms in said quantity thereof are capable of bioremediating said quantity of said explosive material in said explosive device, whereby if said explosive device is installed at a detonation site and fails to detonate as intended, when said quantity of microorganisms is mobilized, said microorganisms in said quantity thereof deactivate said explosive device by bioremediating said quantity of said explosive material in situ at the detonation site.

44. A method as recited in claim 43, further comprising the step of shaping said microorganisms into aggregations having a form selected from the group consisting of a pellet, a capsule, a shard, a flake, a granule, a powder, and a clump.

45. A method as recited in claim 44, wherein said microorganisms are dehydrated.

46. A method as recited in claim 44, wherein said microorganisms are freeze dried.

47. A method as recited in claim 44, wherein said aggregations further comprise a thermal protection additive.

48. A method as recited in claim 43, wherein said explosive material in said explosive apparatus is porous.

49. A method for manufacturing an explosive device capable of self-remediation, if the explosive device fails to detonate as intended, said method comprising the steps:
  (a) selecting an explosive material from which to form an explosive device;
  (b) identifying microorganisms capable of bioremediating said explosive material;
  (c) dispersing a quantity of said microorganisms in a quantity of said explosive material, thereby forming an explosive mixture with bioremediating capacity;
  (d) forming a quantity of said explosive mixture with bioremediating capacity into an explosive device; and
  (e) disposing said quantity of said explosive mixture of said explosive device in a shell, said shell enabling water from the exterior of said shell to flow through said shell into contact with said quantity of said explosive mixture with bioremediating capacity, thereby mobilizing said microorganisms therein, whereby when said quantity of microorganisms in said explosive mixture is mobilized, said microorganisms in said quantity thereof are capable of bioremediating said quantity of said explosive material in said explosive device, and if said explosive device is installed at a detonation site and fails to detonate as intended, said microorganisms in said quantity thereof deactivate said explosive device by bioremediating said quantity of said explosive material in situ at said detonation site.

50. A method as recited in claim 44, wherein said shell is porous.

51. A method for manufacturing an explosive device capable of self-remediation, if the explosive device fails to detonate as intended, said method comprising the steps:
  (a) selecting an explosive material from which to form an explosive device;
  (b) identifying microorganisms capable of bioremediating said explosive material, said microorganisms being among a microorganism consortium identified at the American Type Culture Collection by ATCC Designation No. 55784;
  (c) dispersing a quantity of said microorganisms in a quantity of said explosive material, thereby forming an explosive mixture with bioremediating capacity; and
  d) forming a quantity of said explosive mixture with bioremediating capacity into an explosive device, whereby when said quantity of microorganisms in said explosive mixture is mobilized, said microorganisms in said quantity thereof are capable of bioremediating said quantity of said explosive material in said explosive device, and if said explosive device is installed at a detonation site and fails to detonate as intended, said microorganisms in said quantity thereof deactivate said explosive device by bioremediating said quantity of said explosive material in situ at said detonation site.

52. A method as recited in claim 44, further comprising the step of providing mobilization means for mobilizing said microorganisms to contact said quantity of said explosive material.

53. A method as recited in claim 4, wherein said step of positioning comprises the step of dispersing said microorganisms in said quantity of said explosive material.

54. A method as recited in claim 4, wherein said microorganisms are in an aggregation, and said method further comprises the step of shaping said aggregation into a form selected from the group consisting of a pellet, a capsule, a shard, a flake, a granule, a powder, and a clump.

55. A method as recited in claim 4, wherein said microorganisms are dehydrated.

56. A method as recited in claim 4, wherein said microorganisms are freeze dried.

57. A method as recited in claim 4, wherein said microorganisms are sufficiently resistant to heat that a significant portion of said microorganisms survive when said step of positioning occurs at a temperature of about 100° C.

58. A method as recited in claim 54, wherein said aggregation further comprises thermal protection additives.

59. A method as recited in claim 4, wherein said quantity of said explosive material is porous.

60. A method as recited in claim 20, wherein said shell has an open end, a capwell positioned at said open end, and a bioremediation portal formed through said capwell communicating with said explosive material in said shell.

61. A method as recited in claim 20, wherein said shell is porous.

62. A method as recited in claim 20, wherein said microorganisms are selected from a group of microorganisms consisting of Pseudomonas spp., Escherichia spp., Morganella spp., Rhodococcus spp., Comamonas spp., and denitrifying microorganisms.

63. A method as recited in claim 20, wherein said microorganisms are selected from a group of microorganisms in Pseudomonas spp. consisting of aeruginosa, fluorescens, acidovorans, mendocina, and cepacia.

64. A method as recited in claim 20, wherein said microorganisms are among a microorganism consortium identified at the American Type Culture Collection by ATCC Designation No. 55784.

65. A method as recited in claim 20, further comprising the step of providing mobilization means for mobilizing said microorganisms to contact said quantity of said explosive material.

66. A method as recited in claim 20, wherein said step of positioning comprises the step of dispersing said microorganisms in said quantity of said explosive material.

67. A method as recited in claim 20, wherein said microorganisms are in an aggregation, and said method further comprises the step of shaping said aggregation into a form selected from the group consisting of a pellet, a capsule, a shard, a flake, a granule, a powder, and a clump.

68. A method for manufacturing an explosive device capable of self-remediation, if the explosive device fails to detonate as intended, said method comprising the steps:

(a) forming a quantity of an explosive material into an explosive device;

(b) disposing said quantity of said explosive material in a shell, said shell enabling water from the exterior of said shell to flow through said shell into contact with said quantity of said explosive material;

(c) identifying microorganisms capable of bioremediating said explosive material; and (d) positioning a quantity of said microorganisms in such proximity to said quantity of said explosive material in said explosive device that, when said quantity of microorganisms is mobilized, said microorganisms in said quantity thereof are capable of bioremediating said quantity of said explosive material in said explosive device, whereby if said explosive device is installed at a detonation site and fails to detonate as intended, when said quantity of microorganisms is mobilized, said microorganisms in said quantity thereof deactivate said explosive device by bioremediating said quantity of said explosive material in situ at the detonation site, said microorganisms in said quantity thereof being dehydrated.

69. A method as recited in claim 68, wherein said microorganisms in said quantity thereof are freeze dried.

70. A method as recited in claim 20, wherein said microorganisms are sufficiently resistant to heat that a significant portion of said microorganisms survive when said step of positioning occurs at a temperature of about 100° C.

71. A method as recited in claim 67, wherein said aggregation further comprises thermal protection additives.

72. A method as recited in claim 20, wherein said quantity of said explosive material is porous.

73. A method as recited in claim 49, wherein said shell has an open end, a capwell positioned at said open end, and a bioremediation portal formed through said capwell communicating with said explosive material in said shell.

74. A method as recited in claim 49, wherein said microorganisms are selected from a group of microorganisms consisting of Pseudomonas spp., Escherichia spp., Morganella spp., Rhodococcus spp., Comamonas spp., and denitrifying microorganisms.

75. A method as recited in claim 49, wherein said microorganisms are selected from a group of microorganisms in Pseudomonas spp. consisting of aeruginosa, fluorescens, acidovorans, mendocina, and cepacia.

76. A method as recited in claim 49, wherein said microorganisms are among a microorganism consortium identified at the American Type Culture Collection by ATCC Designation No. 55784.

77. A method as recited in claim 49, further comprising the step of providing mobilization means for mobilizing said microorganisms to contact said quantity of said explosive material.

78. A method as recited in claim 49, wherein said microorganisms are in an aggregation, and said method further comprises the step of shaping said aggregation into a form selected from the group consisting of a pellet, a capsule, a shard, a flake, a granule, a powder, and a clump.

79. A method as recited in claim 49, wherein said microorganisms are dehydrated.

80. A method as recited in claim 49, wherein said microorganisms are freeze dried.

81. A method as recited in claim 49, wherein said microorganisms are sufficiently resistant to heat that a significant portion of said microorganisms survive when said step of positioning occurs at a temperature of about 100° C.

82. A method as recited in claim 78, wherein said aggregation further comprises thermal protection additives.

83. A method as recited in claim 49, wherein said quantity of said explosive material is porous.

84. A method as recited in claim 51, further comprising the step of providing mobilization means for mobilizing said microorganisms to contact said quantity of said explosive material.

85. A method as recited in claim 51, wherein said microorganisms are in an aggregation, and said method further comprises the step of shaping said aggregation into a form selected from the group consisting of a pellet, a capsule, a shard, a flake, a granule, a powder, and a clump.

86. A method as recited in claim 21, wherein said microorganisms are among a microorganism consortium identified at the American Type Culture Collection by ATCC Designation No. 55784.

87. A method as recited in claim 51, wherein said microorganisms are dehydrated.

88. A method as recited in claim 51, wherein said microorganisms are freeze dried.

89. A method as recited in claim 51, wherein said microorganisms are sufficiently resistant to heat that a significant portion of said microorganisms survive when said step of positioning occurs at a temperature of about 100° C.

90. A method as recited in claim 85, wherein said aggregation further comprises thermal protection additives.

91. A method as recited in claim 51, wherein said quantity of said explosive material is porous.

* * * * *

UNITED STATES PATENT AND TRADEMARK OFFICE
CERTIFICATE OF CORRECTION

PATENT NO.      : 6,660,112 B1
DATED           : December 9, 2003
INVENTOR(S)     : Farrell G. Badger et al.

It is certified that error appears in the above-identified patent and that said Letters Patent is hereby corrected as shown below:

Title page,
Item [56], References Cited, OTHER PUBLICATIONS,
"Sidhoum et al.," reference, change "*Alaline*" to -- *Alkaline* --.
"Sidourn, Mohammed, et al.," reference, change "Sidhourn" to -- Sidhoum --.
"Goszczynski, Stefan, et al.," reference, change "pheny-" to -- phenyl- --; and change "1-U-.sup.14" to -- U-.sup.14 --.
"Ziegler, Klaus, et al.," reference, change "Aromitc" to -- Aromatic --.

Column 1,
Line 21, change "5,736,669" to -- 5,763,815 --.
Line 21, change "Apr. 7," to -- Jun. 9, --.
Line 23, change "560,527" to -- 560,074 --.
Line 25, change "5,763,815" to -- 5,736,669 --.

Column 6,
Line 17, change "are not therefore" to -- are not, therefore, --.

Column 9,
Line 58, after "to" delete the period.

Column 12,
Lines 1 and 4, change "interior of neck 40" to -- interior 39 of neck 40 --.

Column 13,
Line 1, change "The" to -- On an extension 68 of shell 62 not surrounding explosive material 66, the --.
Line 13, change "extension of shell 62" to -- extension 68 of shell 62 --.
Line 40, delete "explosive".

Column 15,
Line 54, change "microorganism 30" to -- microorganisms 30 --.

Column 16,
Line 42, change "valve connector 56" to -- valve connector 128 --.
Line 51, change "member 48" to -- member 118 --; and change "second valve member 54" to -- second valve member 124 --.
Line 52, change "first valve 46" to -- first valve 116 --; and change "second valve 52" to -- second valve 122 --.

UNITED STATES PATENT AND TRADEMARK OFFICE
CERTIFICATE OF CORRECTION

PATENT NO. : 6,660,112 B1
DATED : December 9, 2003
INVENTOR(S) : Farrel G. Badger et al.

It is certified that error appears in the above-identified patent and that said Letters Patent is hereby corrected as shown below:

Column 18,
Line 15, change "a" to -- are --.

Column 19,
Line 46, after "suspension" insert -- 214 -- and change "as shown at" to -- shown --.
Line 47, delete "214".
Line 59, after "sufficiently" delete the period.

Column 20,
Line 28, change "materials 30" to -- materials 208 --.

Column 21,
Lines 20 and 21, change "shell 62" to -- shell 206 --.
Line 61, change "PPM" to -- ppm --.

Column 23,
Line 40, change "insufficient particularly" to -- insufficient, particularly --.

Column 25,
Line 11, change "Table 7, below." to -- Table 7 below. --.
Line 55, change "52°" to -- 52° C. --.

Column 26,
Line 1, change "37°" to -- 37° C. --.
Line 3, change "30°" to -- 30° C. --.

Column 27,
Line 7, change "Table 9, below." to -- Table 9 below. --.
Line 35, change "Example 9, above," to -- Example 9 above, --.
Line 45, change "Table 10, below." to -- Table 10 below. --.

Column 28,
Line 31, change "Example, 8, above" to -- Example 8 above --.

Column 29,
Line 3, change "of Example 8, above." to -- of Example 8 above. --.
Line 11, change "Thus" to -- Thus, --.
Line 18, change "only as illustrated" to -- as illustrative only --.

UNITED STATES PATENT AND TRADEMARK OFFICE
CERTIFICATE OF CORRECTION

PATENT NO. : 6,660,112 B1
DATED : December 9, 2003
INVENTOR(S) : Farrel G. Badger et al.

It is certified that error appears in the above-identified patent and that said Letters Patent is hereby corrected as shown below:

Column 30,
Line 40, change "intended" to -- intended, --.
Line 51, before "method" insert -- A --.

Column 32,
Line 55, after "housing" delete the period.

Column 34,
Line 46, change "claim 44" to -- claim 49 --.

Column 35,
Line 6, change "claim 44" to -- claim 4 --.

Signed and Sealed this

Sixth Day of December, 2005

JON W. DUDAS
*Director of the United States Patent and Trademark Office*